United States Patent [19]

Diab et al.

[11] Patent Number: 6,088,607
[45] Date of Patent: Jul. 11, 2000

[54] LOW NOISE OPTICAL PROBE

[75] Inventors: Mohamed Kheir Diab; Massi E. Kiani, both of Laguna Niguel; James M. Lepper, Jr., Trabuco Canyon, all of Calif.

[73] Assignee: Masimo Corporation, Irvine, Calif.

[21] Appl. No.: 08/790,674

[22] Filed: Jan. 28, 1997

Related U.S. Application Data

[63] Continuation of application No. 08/333,132, Nov. 1, 1994, Pat. No. 5,638,818, which is a continuation-in-part of application No. 07/672,890, Mar. 21, 1991, abandoned.

[51] Int. Cl.[7] ...................................................... A61B 5/00
[52] U.S. Cl. .......................................... 600/322; 600/323
[58] Field of Search ........................... 600/300, 322–320, 600/323, 327, 310; 356/41

[56] References Cited

U.S. PATENT DOCUMENTS

| | | |
|---|---|---|
| 2,567,926 | 9/1951 | Dunkelberger . |
| 3,103,214 | 9/1963 | Smith . |
| 3,463,142 | 8/1969 | Harte . |
| 3,482,565 | 12/1969 | Gowen . |
| 3,704,706 | 12/1972 | Herczfeld et al. . |
| 4,129,124 | 12/1978 | Thalmann . |
| 4,321,930 | 3/1982 | Jobsis et al. . |
| 4,334,544 | 6/1982 | Hill et al. . |
| 4,350,165 | 9/1982 | Striese . |
| 4,380,240 | 4/1983 | Jobsis et al. . |
| 4,406,289 | 9/1983 | Wesseling et al. . |
| 4,528,986 | 7/1985 | Arundel et al. . |
| 4,621,643 | 11/1986 | New, Jr. et al. . |
| 4,700,708 | 10/1987 | New, Jr. et al. . |
| 4,824,242 | 4/1989 | Frick et al. . |
| 4,825,872 | 5/1989 | Tan et al. . |
| 4,825,879 | 5/1989 | Tan et al. . |
| 4,830,014 | 5/1989 | Goodman et al. . |
| 4,859,057 | 8/1989 | Taylor et al. . |
| 4,865,038 | 9/1989 | Rich et al. . |
| 4,867,165 | 9/1989 | Noller . |
| 4,880,304 | 11/1989 | Jaeb et al. . |
| 4,907,594 | 3/1990 | Muz . |
| 4,913,150 | 4/1990 | Cheung et al. . |
| 4,927,264 | 5/1990 | Shiga et al. . |
| 4,928,691 | 5/1990 | Nicolson et al. . |
| 4,938,218 | 7/1990 | Goodman et al. . |
| 5,031,608 | 7/1991 | Weinstein . |
| 5,058,588 | 10/1991 | Kaestle . |
| 5,080,098 | 1/1992 | Willett et al. . |
| 5,099,842 | 3/1992 | Mannheimer et al. . |
| 5,109,848 | 5/1992 | Thomas et al. . |
| 5,109,849 | 5/1992 | Goodman et al. . |
| 5,125,403 | 6/1992 | Culp . |
| 5,170,786 | 12/1992 | Thomas et al. . |
| 5,217,013 | 6/1993 | Lewis et al. . |
| 5,224,478 | 7/1993 | Sakai et al. . |
| 5,246,003 | 9/1993 | DeLonzor . |
| 5,337,744 | 8/1994 | Branigan . |
| 5,452,717 | 9/1995 | Branigan et al. . |
| 5,469,845 | 11/1995 | DeLonzor et al. . |

FOREIGN PATENT DOCUMENTS

| | | |
|---|---|---|
| 074428 | 3/1983 | European Pat. Off. . |
| 104772 | 4/1984 | European Pat. Off. . |
| 404562 | 12/1990 | European Pat. Off. . |
| 92/01894 | 2/1992 | WIPO . |

*Primary Examiner*—Robert L. Nasser
*Attorney, Agent, or Firm*—Knobbe, Martens, Olson & Bear LLP

[57] ABSTRACT

An optical probe for measurements, which is particularly suited to reduce noise in measurements taken on an easily compressible material, such as a finger, a toe, a forehead, an earlobe, or a lip. The probe includes a base having an aperture which leads to a chamber. The base is placed adjacent a portion of the material, the chamber being placed directly adjacent any easily compressible portion of the material. A photodetector is located within the chamber and does not contact the material. A light emitting diode (LED) is affixed to the material, opposite the photodetector and above the chamber. The material which is supported by the aperture and therefore rests above or has intruded into the chamber is inhibited from compression since nothing comes in contact with this portion of the material, even when the material moves. Thus, light from the LED is directed through a stabilized portion of the material, i.e., the optical path length through which light travels is stabilized, even during motion of the material. This reduces noise in the signal measured by the photodetector. A scattering medium is interposed between the LED and the material, between the material and the photodetector, or between the LED and the material as well as between the material and the photodetector. The scattering medium is used to improve the signal-to-noise ratio of the received optical signal.

9 Claims, 13 Drawing Sheets

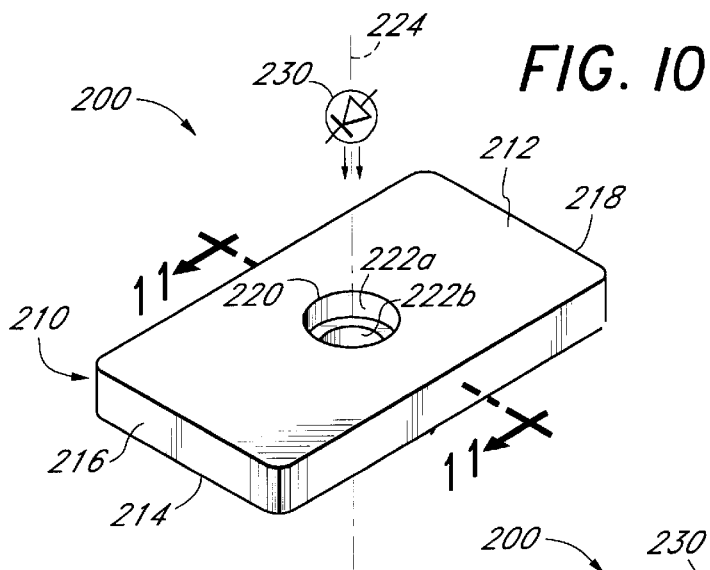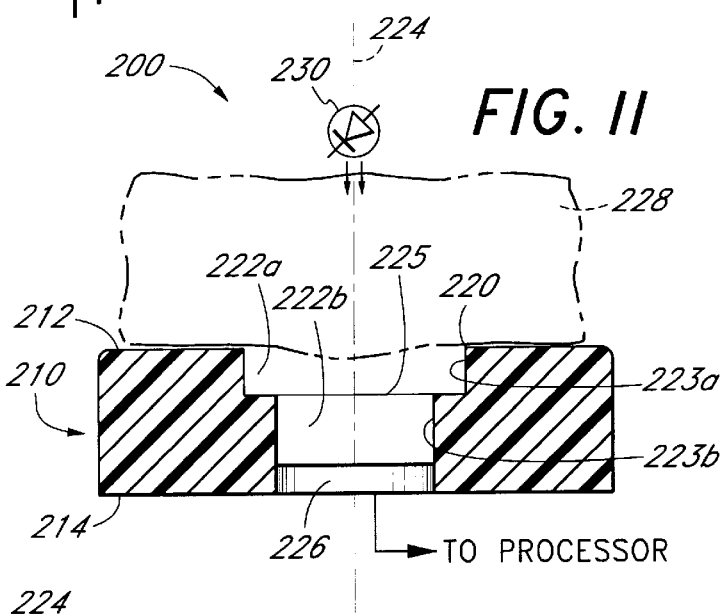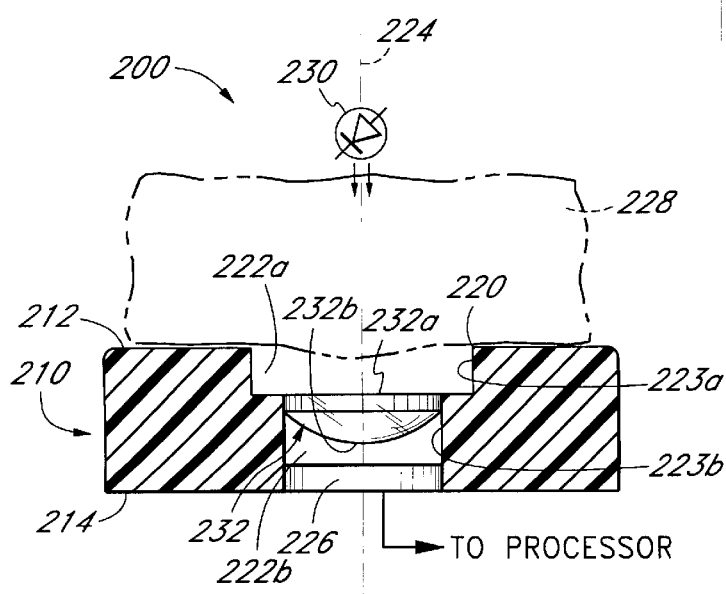

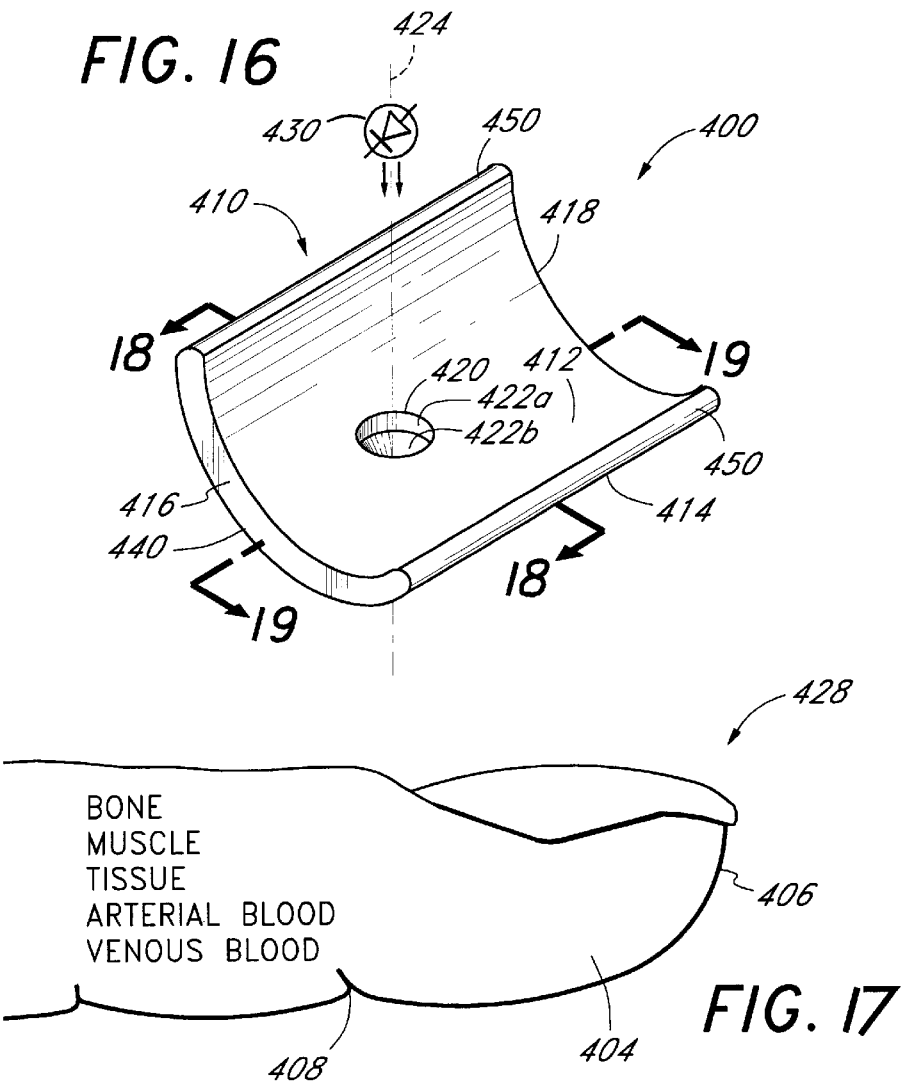

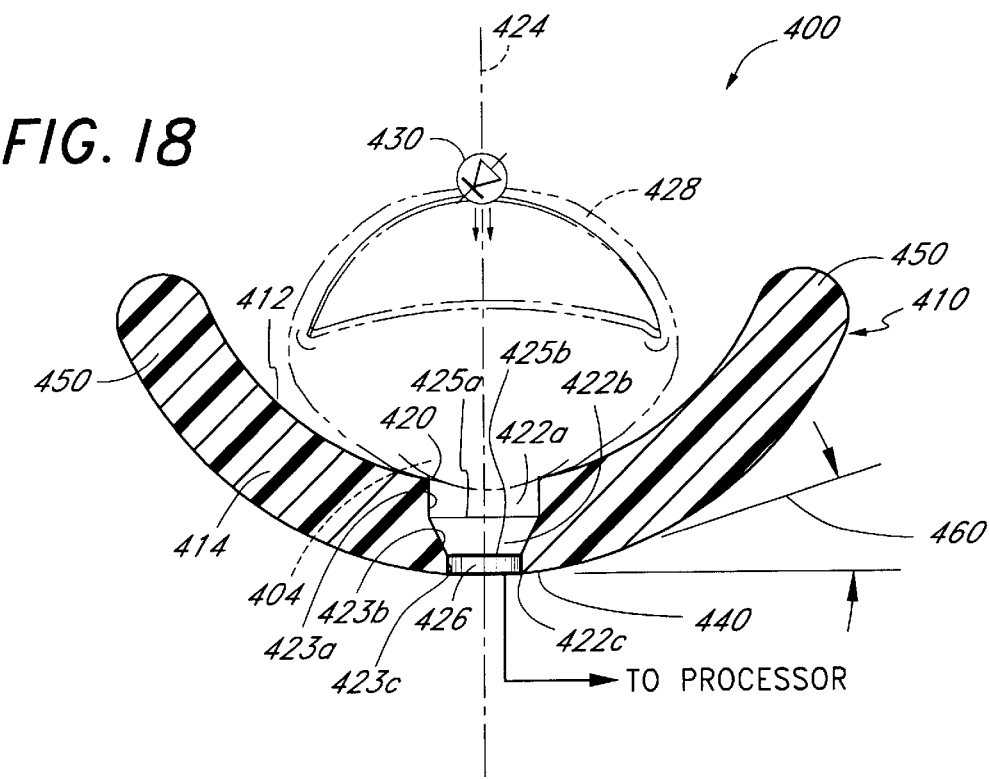
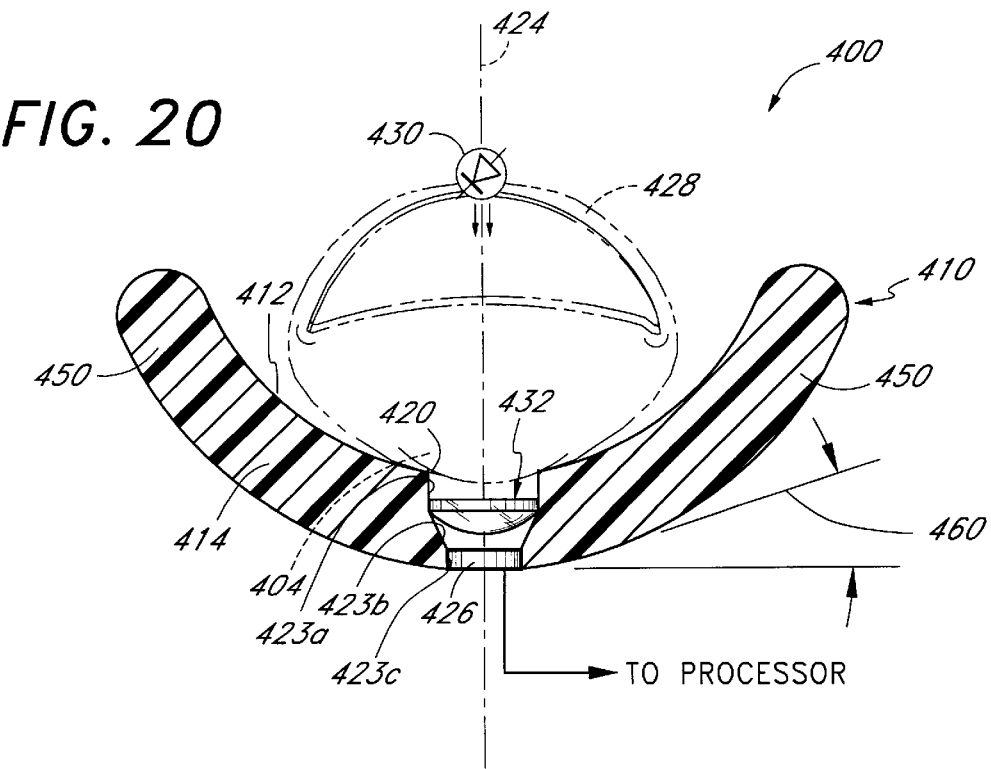

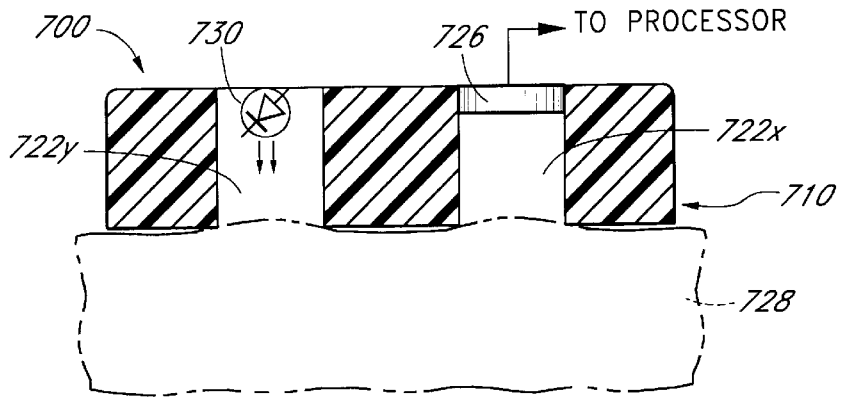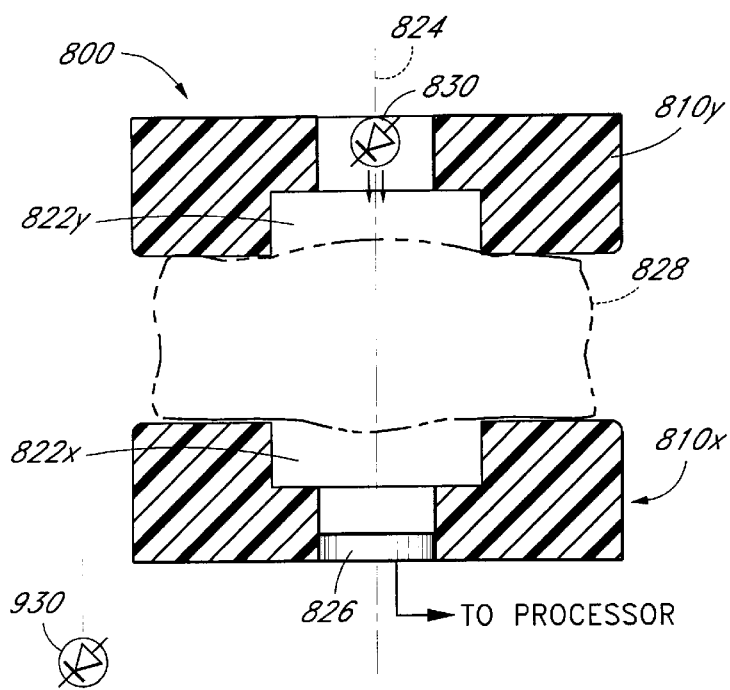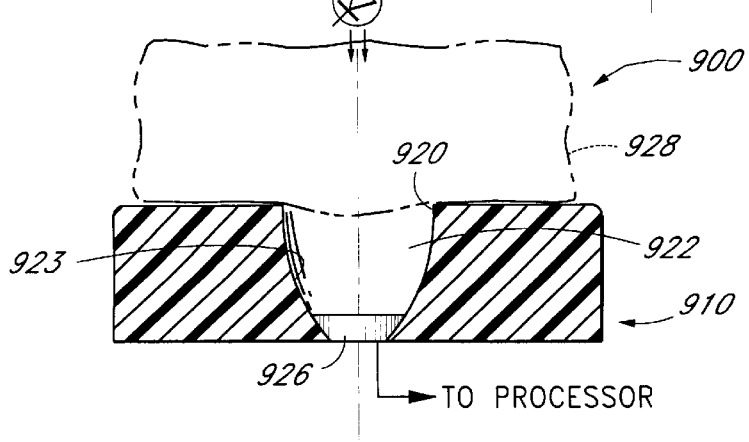

LOW NOISE OPTICAL PROBE

This application is a continuation of U.S. patent application Ser. No. 08/333,132, filed Nov. 1, 1994 now U.S. Pat. No. 5,638,818 which is a continuation-in-part of U.S. patent application Ser. No. 07/672,890, filed Mar. 21, 1991, now abandoned.

BACKGROUND OF THE INVENTION

1. Field of the Invention

The present invention relates to the sensing of energy. More specifically, the present invention relates to the reduction of noise in signals via an improved sensing mechanism.

2. Description of the Related Art

Energy is often transmitted through or reflected from a medium to determine characteristics of the medium. For example, in the medical field, instead of extracting material from a patient's body for testing, light or sound energy may be caused to be incident on the patient's body and transmitted (or reflected) energy may be measured to determine information about the material through which the light has passed. This type of non-invasive measurement is more comfortable for the patient and can be performed more quickly.

Non-invasive physiological monitoring of bodily function is often required. For example, during surgery, blood pressure and the body's available supply of oxygen, or the blood oxygen saturation, are often monitored. Measurements such as these are often performed with non-invasive techniques where assessments are made by measuring the ratio of incident to transmitted (or reflected) light through a portion of the body, for example a digit such as a finger, or an earlobe, or a forehead.

Transmission of optical energy as it passes through the body is strongly dependent on the thickness of the material through which the light passes, or the optical path length. Many portions of a patient's body are typically soft and compressible. For example, a finger comprises skin, muscle, tissue, bone, blood, etc. Although the bone is relatively incompressible, the tissue, muscle, etc. are easily compressible with pressure applied to the finger, as often occurs when the finger moves. Thus, if optical energy is made incident on a finger and the patient moves in a manner which distorts or compresses the finger, the optical path length changes. Since a patient generally moves in an erratic fashion, the compression of the finger is erratic. This causes the change in optical path length to be erratic, making the absorbtion erratic, resulting in a difficult to interpret measured signal.

Many types of non-invasive monitoring devices have been developed to try to produce a clear and discernable signal as energy is transmitted through a medium, such as a finger or other part of the body. In typical optical probes a light emitting diode (LED) is placed on one side of the medium while a photodetector is placed on an opposite side of the medium. Many prior art optical probes are designed for use only when a patient is relatively motionless since, as discussed above, motion induced noise can grossly corrupt the measured signal. Typically, probes are designed to maximize contact between the LED and the medium and the photodetector and the medium to promote strong optical coupling between the LED, the medium, and the photodetector, thereby generating a strong output signal intensity. In this way, a strong, clear signal can be transmitted through the medium when the patient is generally motionless.

For example, U.S. Pat. No. 4,880,304 to Jaeb, et al. discloses an optical probe for a pulse oximeter, or blood oxygen saturation monitor, comprising a housing with a flat lower face containing a central protrusion in which a plurality of light emitting diodes (LEDs) and an optical detector are mounted. When the probe is placed on the patient's tissue, the protrusion causes the LEDs and the detector to press against the tissue to provide improved optical coupling of the sensor to the skin. In another embodiment (FIGS. 4a and 4b in the Jaeb patent), the LEDs and the detector are arranged within a central chamber, generally horizontal with respect to the tissue on which the probe is placed. A set of mirrors or prisms causes light to be directed from the LEDs onto the tissue through a polymer sealant within the chamber, the sealant providing a contact with the tissue for good optical coupling with the tissue.

U.S. Pat. No. 4,825,879 to Tan, et al. discloses an optical probe wherein a T-shaped wrap, having a vertical stem and a horizontal cross bar, is utilized to secure a light source and an optical sensor in optical contact with a finger. The light source is located in a window on one side of the vertical stem while the sensor is located in a window on the other side of the vertical stem. The finger is aligned with the stem and the stem is bent such that the light source and the sensor lie on opposite sides of the finger. Then, the cross bar is wrapped around the finger to secure the wrap, thereby ensuring that the light source and the sensor remain in contact with the finger to produce good optical coupling.

U.S. Pat. No. 4,380,240 to Jöbsis, et al. discloses an optical probe wherein a light source and a light detector are incorporated into channels within a slightly deformable mounting structure which is adhered to a strap. Annular adhesive tapes are placed over the source and the detector. The light source and detector are firmly engaged with a bodily surface by the adhesive tapes and pressure induced by closing the strap around a portion of the body. An alternative embodiment provides a pressurized seal and a pumping mechanism to cause the body to be sucked into contact with the light source and detector.

U.S. Pat. No. 4,865,038 to Rich, et al. discloses an optical probe having an extremely thin cross section such that it is flexible. A die LED and a die photodetector are located on a flexible printed circuit board and encapsulated by an epoxy bead. A spacer, having circular apertures positioned in alignment with the LED and photodetector, is placed over the exposed circuit board. A transparent top cover is placed over the spacer and is sealed with a bottom cover placed under the circuit board, thereby sealing the probe from contaminants. A spine may be added to strengthen the device. The flexibility of the device allows it to be pinched onto the body causing the epoxy beads over the LED and the photodetector to protrude through the apertures in the spacer and press against the top cover such that good optical contact is made with the body.

U.S. Pat. No. 4,907,594 to Muz discloses an optical probe wherein a dual wall rubberized sheath is fit over a finger. A pump is located at the tip of the finger such that a pressurized chamber may be formed between the two walls, thereby causing an LED and a photodetector located in the inner wall to be in contact with the finger.

Each of the above described optical probes is designed to cause a strong measured signal at the photodetector by optimizing contact between the LED, the patient, and the probe. However, this optimization forces compressible portions of the patient's body to be in contact with surfaces which compress these portions of the patient's body when the patient moves. This can cause extreme changes in the thickness of material through which optical energy passes, i.e., changes in the optical path length and changes due to scattering as a result of venous blood movement during motion. Changes in the optical path length can produce enough distortion in the measured signal to make it difficult or impossible to determine desired information. Thus, a need exists for a probe which inhibits motion induced noise, or motion artifacts, during measurement of a signal while still generating a transmitted or reflected signal of sufficient intensity to be measured by a detector.

SUMMARY OF THE INVENTION

The present invention involves a probe for use in both invasive and non-invasive energy absorption (or reflection) measurements. A base is formed in a shape generally corresponding to the material on which measurements are to be made, for example, a section of a patient's body such as a finger, an earlobe, a forehead, a toe, an organ, or a portion of tissue. The base has a forward end, a rear end, a top and a bottom. An aperture is formed in the top of the base. The aperture is the entrance to a chamber. A detector, such as a photodetector, is mounted within the chamber, typically in the bottom of the chamber. The material on which measurements are to be made is placed on the base such that any compressible portion of the material is located directly adjacent the chamber. Thus, the compressible portion of the material is caused to rest above or enter into the chamber. The chamber is deep enough that any material which intrudes into the chamber does not contact anything which might cause compression.

A light source, such as an LED, is affixed to the material, opposite the photodetector. The LED emits light energy which propagates through and is absorbed by the material along the optical path length, or thickness of material through which light propagates. An attenuated light energy signal emerges from the material, into the chamber. As light propagates through the material, it is scattered by the material and is thus transmitted into the chamber over a broad range of angles. The photodetector produces an electrical signal indicative of the intensity of the signal transmitted by the material. The electrical signal is input to a processor which analyzes the signal to determine information about the medium through which light energy has been transmitted.

The probe of the present invention has an aperture and chamber which enable an easily compressible portion of the material that light energy passes through to rest in the chamber and not be compressed. This results in less disturbance of the optical path between the light source and the detector. Since the LED is generally aligned with the chamber and the photodetector, the light energy signal propagates through the portion of the material which rests above or is accommodated within the chamber. The chamber allows the compressible portion of the material to remain substantially uncompressed, even during motion, since nothing within the chamber physically contacts the material through which light energy passes to cause compression. Thus, the thickness of the material, or the optical path length, is stabilized, and the movement of venous blood during motion is minimized, thereby improving the signal-to-noise ratio of the measured signal. Thus, the probe of the present invention produces a strong, clear signal wherein noise due to motion, or motion artifacts, is substantially reduced.

In one preferred embodiment of the present invention, the chamber is filled with a scattering medium. The scattering medium is advantageously formed of a conformable plastic or a highly compressible material so that the material on which measurements are to be made is not compressed upon contact with the scattering medium. The scattering medium helps to minimize the effects of local artifacts and perturbations within the material. Thus, an increased optical signal-to-noise ratio is observed. The scattering medium also improves the optical coupling with the material.

In another preferred embodiment, the scattering medium is interposed between the light source and the material, and in yet another preferred embodiment, the scattering medium is interposed between the light source and the material as well as between the material and the photodetector. Each of these embodiments results in an improved optical signal-to-noise ratio.

In yet another preferred embodiment, an immersion lens is utilized in combination with the light source and/or the photodetector. In a particularly preferred embodiment, the immersion lens is formed by placing an epoxy bump forming a partial sphere over semiconductor diodes used as the light source and/or the photodetector to improve the signal-to-noise ratio.

BRIEF DESCRIPTION OF THE DRAWINGS

FIG. 10 is a perspective view of another embodiment of a probe of the present invention having a two segment chamber.

FIG. 11 is a cross-sectional view of another embodiment of the probe of FIG. 10 incorporating a two segment chamber having a detector within it.

FIG. 12 is a cross-sectional view of another embodiment of the probe of FIG. 10 incorporating a light collecting lens in a two segment chamber.

FIG. 16 is a perspective view of a probe of the present invention specifically designed to be used with a digit.

FIG. 17 illustrates a schematic finger comprising fingernail, skin, bone, tissue, muscle, blood, etc.

FIG. 18 is a cross-section view of the probe of FIG. 16.

FIG. 19 is a longitudinal cross-sectional view of the probe of FIG. 16.

FIG. 20 is a cross-sectional view of another embodiment of the probe of FIG. 16 incorporating a light collecting lens.

FIG. 21 is a cross-sectional view of a probe of the present invention designed to be utilized for reflectance measurements.

FIG. 22 is a cross-sectional view of a probe which is advantageously used for non-invasive measurements when a material is compressible on more than one side. The probe has two bases, each with a chamber to house a detector or an energy source and thereby reduce motion artifacts.

FIG. 23 is a cross-sectional view of a probe having a generally cone-shaped chamber with a reflective surface which advantageously causes energy to be concentrated, or "funneled," onto the surface of a detector within the chamber, improving the measured signal.

DETAILED DESCRIPTION OF THE INVENTION

Examination of a material is often advantageous, especially when it is difficult or expensive to procure and test a sample of the material. For example, in physiological measurements, it is often desirable to monitor a patient without unnecessary drawing of blood or tissue from the patient. The known properties of energy absorption as energy propagates through a material may be used to determine information about the material through which the energy has passed. Energy is made incident on a material, and a measurement is made of energy either transmitted by or reflected from the material.

Figure 1:
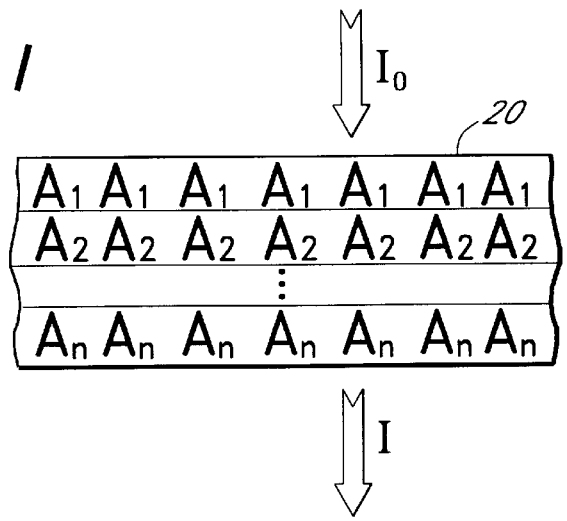
FIG. 1 illustrates a schematic medium comprising N different constituents.

The amplitude of the measured signal is highly dependent on the thickness of the material through which the energy passes, or the optical path length, as well as other properties such as the erratic movement of venous blood during motion. A schematic medium 20 comprising N different constituents $A_1$ through $A_N$ is shown in FIG. 1. Energy transmitted through the medium 20 is approximately attenuated according to the equation:

$$I = I_0 e^{-\sum_{i=1}^{N} \epsilon_i c_i x_i} \quad (1)$$

where $\epsilon_i$ is the absorption coefficient of the $i^{th}$ constituent; $x_i$ is the thickness of the $i^{th}$ constituent through which light energy passes, or the optical path length of the $i^{th}$; and $c_i$ is the concentration of the $i^{th}$ constituent in thickness $x_i$.

Since energy absorption is strongly dependent on the thicknesses of the constituents $A_1$ through $A_N$ which make up the medium 20 through which the energy passes, when the thickness of the medium 20 changes, due to motion for example, the thicknesses of the individual constituents $A_1$ through $A_N$ change. This causes the absorption characteristics of the medium 20 to change.

Often a medium 20 is under random or erratic motion. For example, if the medium 20 is an easily compressible portion of a patient's body, such as a digit, and the patient moves, the medium 20 compresses erratically causing the individual thicknesses $X_1$ through $X_N$ of the constituents $A_1$ through $A_N$ to vary erratically. This erratic variation may cause large excursions in the measured signal and can make it extremely difficult to discern a desired signal, as would be present without motion induced noise, or motion artifacts.

Figure 2A:
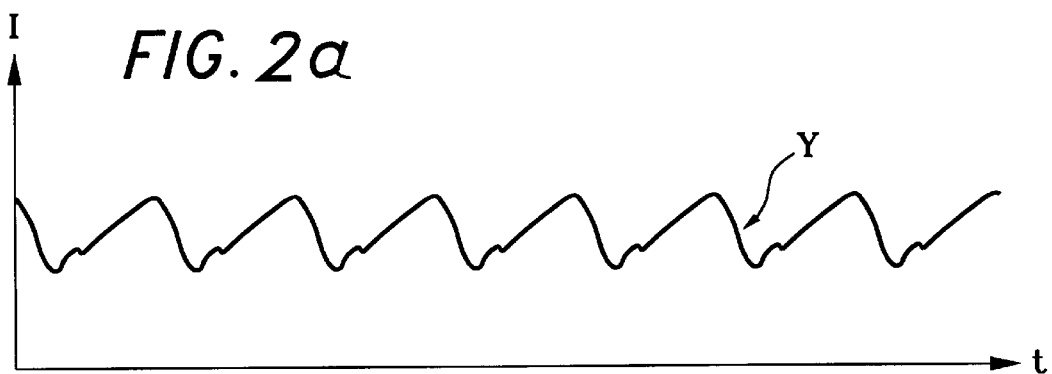
FIG. 2a illustrates an ideal plethysmographic signal that would be measured by the optical probe of the present invention when utilized for pulse oximetry.
Figure 2B:
FIG. 2b illustrates a realistic signal measured by the optical probe of the present invention when utilized for pulse oximetry.

For example, FIG. 2a illustrates an ideal desired signal waveform, labelled Y, measured in one application of the present invention, namely pulse oximetry. FIG. 2b illustrates a more realistic measured waveform S, also measured in a pulse oximetry application, comprising the ideal desired signal waveform Y plus motion induced noise, n, i.e. S=Y+n. It is easily seen how motion artifacts obscure the desired signal portion Y.

Figure 3:
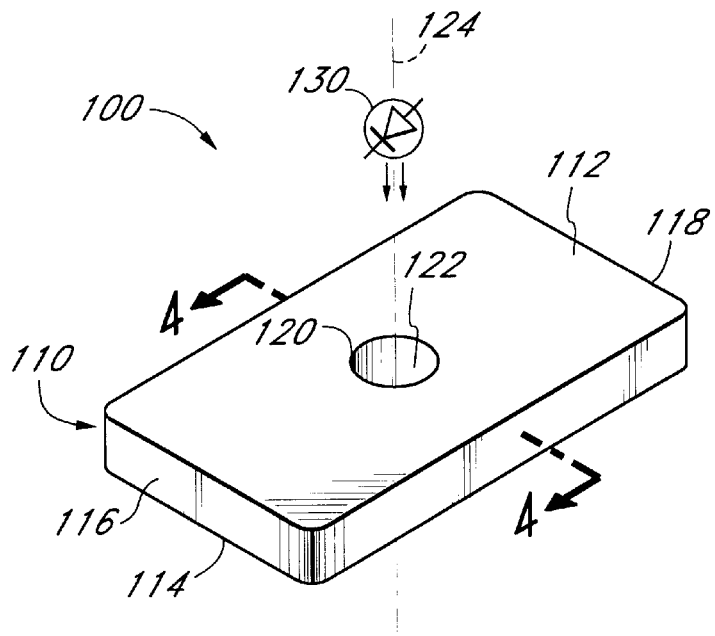
FIG. 3 is a perspective view of a probe of the present invention having a single segment chamber.
Figure 4:
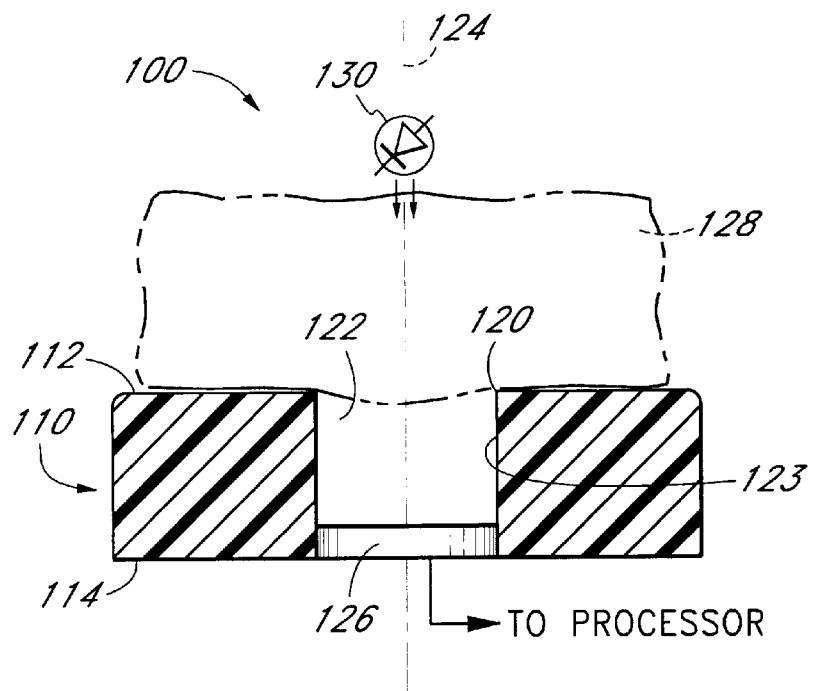
FIG. 4 is a cross-sectional view of an optical probe of the present invention illustrating a single segment chamber having a detector within it.

FIG. 3 is a perspective view of one embodiment of an optical probe 100 of the present invention which greatly diminishes the effects of motion artifacts on the measured signal. FIG. 4 shows a cross-sectional view of the optical probe 100 of the present invention taken along line 4—4 in FIG. 3. For clarity in the perspective view of FIG. 3, a material 128 on which measurements are to be taken is not shown placed adjacent the probe 100. However, the material 128 on which measurements are to be made is shown in FIG. 4. As illustrated in FIGS. 3 and 4, a base 110, having a top 112, a bottom 114, a forward end 116, and a rear end 118, is made of a material which is preferably rigid and opaque. It will be understood, however, that the probe 100 may be made of materials which may be rigid, resilient, opaque, or transparent, for example.

An aperture 120 is formed in the top 112 of the base 110. Typically, the aperture 120 is located at a point between one-quarter and one-half of the length of the base 100. The aperture 120 may be of any shape, including but not limited to circular, square, or triangular. The aperture 120 forms the opening to a chamber 122 which may also be of any shape. In one embodiment, a lateral cross-section (not shown) of the chamber 122 is the same shape as the aperture. A central axis 124 of the chamber 122 is defined by a line aligned perpendicular to the aperture 120 and extending generally through a central portion of the aperture 120.

In the embodiment of FIG. 4, a light source 130, typically a light emitting diode (LED), is affixed adjacent the material 128, aligned along the central axis 124 of the chamber 122 opposite the chamber 122. Typically, an adhesive such as medical tape is used to affix the LED 130 to the material 128. A detector 126, such as a photodetector, is placed within the chamber 122. A central portion of the photodetector 126 is generally aligned with the central axis 124 of the chamber 122, typically at the bottom 114 of the chamber 122. The photodetector 126 may be fixed within the chamber 122 according to a number of different methods, including but not limited to adhesive, a press fit, or clear epoxy resin which transmits light over a range of wavelengths of interest. Typically, no matter how the photodetector 126 is held within the chamber 122, the bottom surface 114 of the chamber 122 is made opaque either via the press fit or via paint or tape, for example.

It is often the case that materials 128 on which absorption measurements are performed are, at least in part, easily compressible. Easily compressible portions of the material 128 is placed directly adjacent (i.e., above) the chamber 122. The area surrounding the aperture 120 supports the material covering the chamber 122. The chamber 122 is wide enough that any compressible portion of the material 128 located above the aperture 120 may intrude into the chamber 122. Thus, the material 122 may rest above or penetrate slightly into the chamber 122 and is thereby shielded from perturbations which compress the material 128, such as pressure caused when the material 128 is touched.

In the present embodiment, the depth of the chamber 122 may range from 0.5 mm to 10 mm in depth, with 2–4 mm preferred, and 3–4 mm more preferred. Similarly, the diameter of the aperture 120 may, in the present embodiment, range from 3 mm to 20 mm, as required by the specific application. For instance, the aperture would be smaller for neonates than for adults. These sizes have been found to be effective in reducing perturbations and compression of the material 128, when the material is human skin.

The chamber 122 is deep enough that the photodetector 126 and the bottom 114 of the chamber 122 do not come into contact with the easily compressible portion of the material 128, even when the material 128 is caused to move. Thus, along the central axis 124 of the chamber 122 nothing comes into physical contact with the easily compressible portion of the material 128 and causes it to compress. With little or no compression of the material 128 in this region, the thickness of the material 128, or the optical path length of light energy propagating through the material 128, is substantially stabilized in the field of view of the photodetector. The movement of venous blood due to compression is also minimized in the field of view of the photodetector.

The LED 130 emits light at a known wavelength. The light propagates through the material 128 and an attenuated signal is transmitted into the chamber 122 to be received by the photodetector 126. As light from the LED 130 propagates through the material 128, it is scattered by the material 128 and is thus transmitted into the chamber 122 over a broad range of angles in a very complex manner. Thus, some of the light is caused to be incident on the opaque walls 123 of the chamber 122 and is absorbed. Although the signal travels through a greater optical distance to reach the photodetector 126 at the bottom 114 of the chamber 122 than if the photodetector 126 were immediately adjacent the material 128, thus eliminating direct coupling between the photodetector 126 and the material 128, the resulting degradation to signal intensity is compensated for by the stabilization of the optical path length and the resultant reduction of noise in the measured signal. The photodetector 126 produces an electrical signal indicative of the intensity of light energy incident on the photodetector 126. The electrical signal is input to a processor which analyzes the signal to determine characteristics of the media 128 through which the light energy has passed.

The opaque quality of the base 110 absorbs ambient light which can interfere with the signal measured at the photodetector 126. This further improves signal quality. Further, the opaque bottom 114 of the chamber 122 protects the photodetector 126 from ambient light which can obscure the desired signal measured at the photodetector 126. Thus, an accurate measurement of the intensity of the attenuated signal may be made at the photodetector 126.

Figure 5:
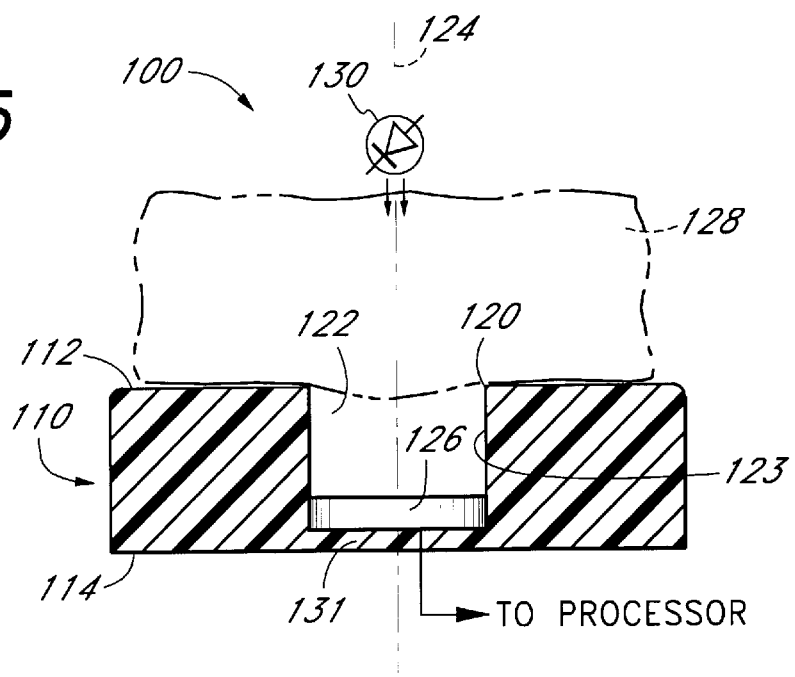
FIG. 5 is a cross-sectional view of a probe of the present invention having a detector resting on a shell of base material.

An alternative embodiment of the chamber 122 is shown in frontal cross-section in FIG. 5. A shell 131 of base 110 material covers the bottom 114 of the chamber 122. The photodetector 126 is mounted on the shell 131, within the chamber 122, generally aligned with the LED 130. The photodetector 126 is electrically connected to a processor through a small hole (not shown) in the shell 131. The shell 131 shields the photodetector 126 from ambient light which can seriously degrade the signal-to-noise ratio of the signal measured at the photodetector 126. It will be understood that the bottom 114 of the chamber 122 may be formed with or without the shell in any embodiment of the probe of the present invention.

Figure 6:
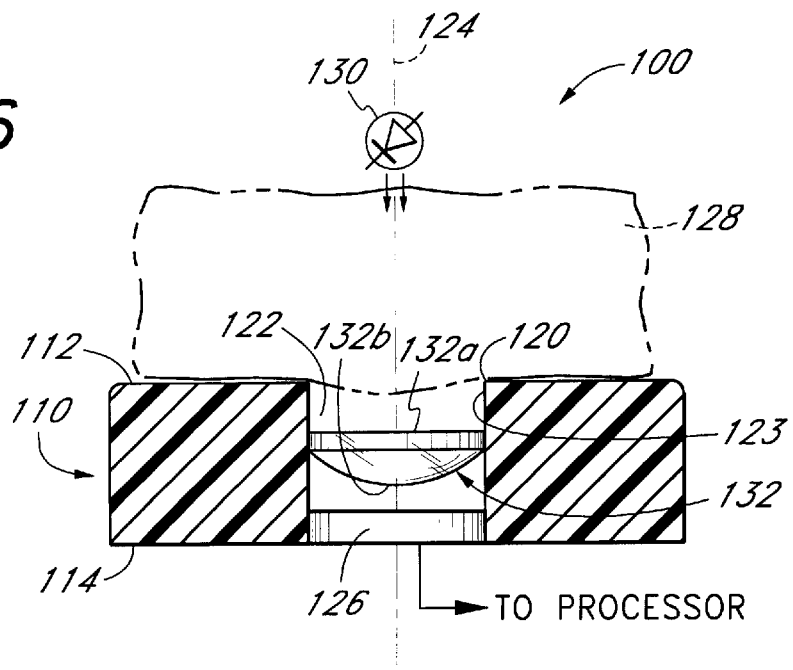
FIG. 6 is a cross-sectional view of a probe of the present invention incorporating a light collecting lens.

FIG. 6 shows a frontal cross sectional view of another embodiment of the probe 100 of the present invention wherein a light collecting lens 132 is placed within the chamber 122, between the material 128 which rests above or enters into the chamber 122 and the photodetector 126. The lens 132 has one generally planar surface 132a aligned parallel to the aperture 120 in the top 112 of the base 110, located deep enough within the chamber 122 that any material 128 which intrudes into the chamber 122 does not contact the planar surface 132a of the lens 132. Another surface 132b of the lens 132 is generally convex having its apex directed toward the photodetector 126 in the bottom 114 of the chamber 122. The lens 132 may be held in the chamber 122 by a number of means, including but not limited to optical adhesive, a lens retaining ring, or a press fit. The chamber 122 functions in the same manner as described above to stabilize the optical path length and reduce motion artifacts. The light collecting lens 132 gathers much of the light which was scattered as it was transmitted through the material 128 and causes it to be incident on the photodetector 126. This produces a stronger measured signal.

Figure 7:
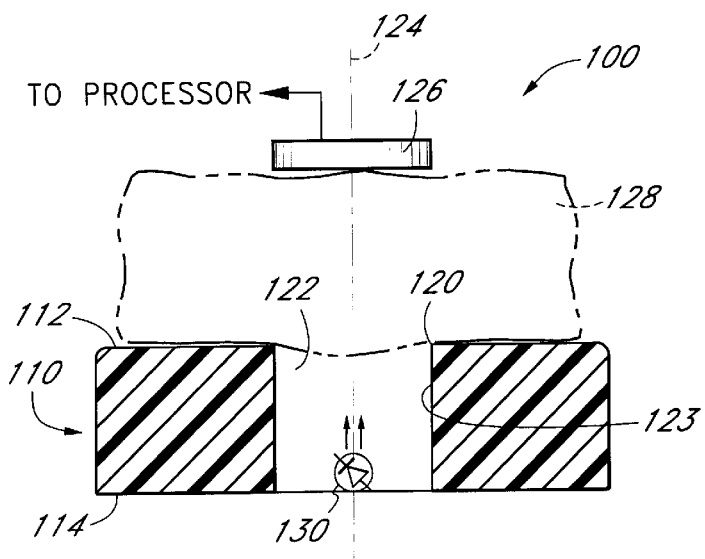
FIG. 7 is a cross-sectional view of a probe of the present invention illustrating a single segment chamber having an LED within it.

FIG. 7 shows another embodiment of the probe 100 of the present invention wherein the positions of the photodetector 126 and the LED 130 are interchanged. The LED 130 is placed within the chamber 122, typically at the bottom 114 of the chamber 122, generally aligned with the central axis 124 of the chamber 122. The LED 130 may be fixed within the chamber 122 according to a number of different methods, including but not limited to a press fit, adhesive, or clear epoxy resin which transmits light over a range of wavelengths of interest, such as around the wavelength which the LED emits. Again, a material 128 is placed on the base 110 having a compressible portion of the material 128 located directly above the chamber 122. The photodetector 126 is attached to the material 128, opposite the LED 130, such that the LED 130, the photodetector 126, and the chamber 122 are aligned along the central axis 124 of the chamber 122. The photodetector 126 is typically attached by an opaque material. For example, the photodetector 126 may be attached to the material 128 with opaque tape, thereby limiting signal degradation caused by ambient light. The photodetector 126 is, again, electrically connected to a processor.

The probe 100 of this embodiment functions substantially identically to the embodiment of the probe 100 having the photodetector 126 housed in the chamber 122. The chamber 122 stabilizes the optical path length by allowing easily compressible portions of the material 128 to rest above or intrude into the chamber 122, thereby stabilizing the optical path length and substantially reducing motion artifacts. This is true regardless of whether the photodetector 126 or the LED 130 is housed within the chamber 122.

Figure 8:
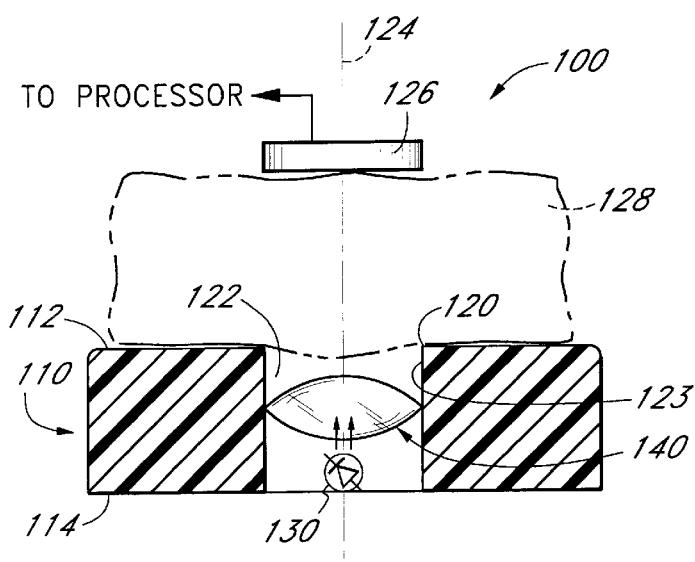
FIG. 8 is a cross-sectional view of a probe of the present invention incorporating a collimating lens assembly.

FIG. 8 shows a cross-sectional view of another embodiment of the probe 100 of the present invention wherein the LED 130 is located within the chamber 122. A collimating lens assembly 140 is placed within the chamber 122, between the material 128 which rests above or enters into the chamber 122 and the LED 130. Collimating lens assemblies 140 are well known in the art and, thus, the lens assembly 140 is represented schematically in the FIG. 8. The collimating lens assembly 140 is located deep enough within the chamber 122 that any material 128 which intrudes into the chamber 122 does not contact the lens assembly 140. The lens assembly 140 may be held in the chamber 122 by a number of means, including but not limited to optical adhesive, a lens retaining ring, or a press fit. The chamber 122 functions in the same manner as described above to stabilize the optical path length and reduce motion artifacts. The collimating lens assembly 140 causes light from the LED 130 to be focused on the material 128 above the chamber 122, thus providing a less scattered signal transmitted onto the photodetector 126 surface, thereby utilizing the photodetector 126 more effectively.

Figure 9:
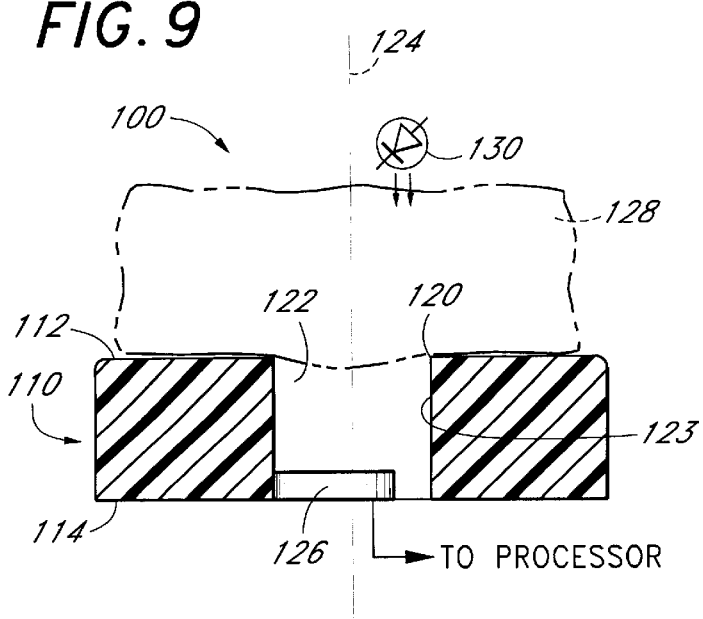
FIG. 9 is a cross-section view of a probe of the present invention wherein the LED and the detector are not aligned along the central axis of the chamber.

FIG. 9 shows another embodiment of the probe 100 of the present invention wherein the LED 130 and the photodetector 126 are not aligned along the central axis 124 of the chamber 122. Light is scattered within the material 128, causing at least a portion of the light emitted by the LED 130 to reach the photodetector 126 for measurement. As long as light emitted by the LED 130 and scattered by the material 128 reaches the photodetector 126 with great enough intensity to be measured, the LED 130 and the photodetector 126 need not be aligned. While alignment of the LED 130 and the photodetector 126 along the same axis causes the light emitted by the LED 130 to reach the photodetector 126 more directly, it is not necessary for operation of the probe of the present invention. In some applications, misalignment may even be advantageous. It will be understood that this is true for any embodiment of the probe of the present invention. Additionally, it will be understood that a photodetector 126 which fills the width of the chamber 122 is advantageous in that more of the light directed into the chamber 122 will be incident on the surface of the photodetector 126, resulting in a stronger measured signal. However, any size photodetector 126 which acquires enough energy to produce an adequately strong measured signal is acceptable. It will be understood that this is true for any embodiment of the probe of the present invention.

A perspective view of another embodiment of a probe 200 of the present invention comprising a multi-segment chamber 222 is shown is FIG. 10. FIG. 11 shows a cross-sectional view of the probe 200 of the present invention taken along line 11—11 in FIG. 10. For clarity in the perspective view of FIG. 10, a material 228 on which measurements are to be taken is not shown placed adjacent the probe 200. However, the material 228 is shown adjacent the probe 200 in FIG. 11.

As illustrated in FIGS. 10 and 11, a base 210, having a top 212, a bottom 214, a forward end 216, and a rear end 218, is made of a material which is preferably rigid and opaque. It will be understood, however, that the probe 200 may be made of materials which may be rigid, resilient, opaque, or transparent, for example. An aperture 220 of any shape is formed in the base 210, similar to the aperture 120 described above in conjunction with the probe 100 of FIGS. 3 through 9. The aperture 220 forms the opening to a stabilizing segment 222a of the multiple segment chamber 222. A lateral cross-section (not shown) of the stabilizing segment 222a of the chamber 222 is typically the same shape as the aperture 220. Walls 223a of the stabilizing segment 222a are generally perpendicular to the aperture 220. A central axis 224 of the chamber 222 is defined by a line aligned generally perpendicular to the aperture 220 and extending generally through a central portion of the aperture 220 and the chamber 222.

A mounting segment 222b is located directly adjacent and below the stabilizing segment 222b, connected to the stabilizing segment 222b by a border 225. The mounting segment 222b shares the central axis 224 of the stabilizing segment 222a and is typically of smaller width. Walls 223b of the mounting segment 222b are generally parallel to the central axis 224. The mounting segment 222b may extend through the bottom 214 of the base 210, as shown in FIG. 11, or the mounting segment 222b may extend to just above the bottom 214 of the base 210, leaving a shell (not shown) of base 210 material at the bottom 214 of the chamber 222.

A photodetector 226 is placed in the mounting segment 222b of the chamber 222, typically at the bottom 214 of the mounting segment 222b, having a central portion of the photodetector 226 generally aligned with the central axis 224 of the chamber 222. The mounting segment 222b of the chamber 222 is deep enough that the photodetector 226 does not penetrate into the stabilizing segment 222 of the chamber 222. The photodetector 226 may be fixed within the chamber 222 according to a number of different methods, including but not limited to adhesive, a press fit, or a clear epoxy resin which transmits light over a range of wavelengths of interest. In this embodiment, the bottom 214 of the chamber 222 is made opaque via paint or tape, for example, or by leaving a shell (not shown) of base 210 material at the bottom 214 of the chamber 222 when the chamber 222 is formed. The photodetector 226 is electrically connected to a processor, similarly to the photodetector 126 in the previous embodiment of the probe 100 of the present invention.

An energy absorbing material 228 (the material under test) is placed over the base 210 as shown in the cross section of FIG. 11. A portion of the material 228 may rest above the chamber 222. Additionally, the stabilizing segment 222a of the chamber 222 is wide enough that any easily compressible portion of the material 228 may intrude into the stabilizing segment 222a of the chamber 222. The stabilizing segment 222a of the chamber 222 is deep enough that the portion of the material 228 which enters into the stabilizing segment 222a does not contact matter within the stabilizing segment 222a which might cause compression, even when the material 228 is caused to move.

A light emitting diode (LED) 230 is affixed adjacent to the material 228, opposite the aperture 220. The LED 230 is advantageously aligned along the central axis 224 to optimize the amount of light incident directly through the material 228 onto the photodetector 226. However, it will be understood that the positions of the photodetector 226 and the LED 230 could be interchanged as discussed in conjunction with FIG. 7. Additionally, a collimating lens assembly (not shown) could be added to the chamber 222 as discussed in conjunction with FIG. 8. The collimating lens assembly may be held in the chamber 222 similarly to a light collecting lens 232 discussed below. Further, it will be understood that the LED 230 and the photodetector 226 could be unaligned, as discussed in conjunction with FIG. 9.

As light from the LED 230 propagates through the material 228, it is scattered by the material 228 and is thus transmitted into the chamber 222 over a broad range of angles. Thus, some of the light is caused to be incident on the opaque walls 223a and 223b of the chamber 222 and is absorbed. However, the advantageous alignment of the photodetector 226 and the LED 230 along the central axis 224 causes a large percentage of the light to be incident on the surface of the photodetector 226. Since the material 228 remains substantially uncompressed above and within the stabilizing segment 222a, the thickness through which the light travels, or the optical path length, is substantially stabilized. Thus, the signal-to-noise ratio of the measured signal is improved by the suppression of motion artifacts due to the chamber 222.

In another embodiment of the probe 200, a light collecting lens 232 is inserted within the chamber 222, as shown in cross-section in FIG. 12. The lens 232 is advantageously supported at the border 225 between the stabilizing segment 222a and the mounting segment 222b. The lens may be held in place by a number of means, including but not limited to an optical adhesive, a lens retaining ring, or a press fit. The lens 232 has a generally planar surface 232a aligned with the border 225 between the stabilizing segment 222a and the mounting segment 222b and a generally convex surface 223b extending into the mounting segment 222b of the chamber 222. The stabilizing segment 222a of the chamber 222 is deep enough that the lens 232 does not contact any of the compressible material 228 which may have intruded into the chamber 222.

The lens 232 collects light which is incident on the planar surface 232a. Much of the light which is incident on this surface 232a at angles which would be absorbed by the walls 223a and 223b of the chamber 222 if the lens were not present is now directed toward the photodetector 226. Thus, a greater percentage of the light transmitted through the material 228 is caused to be incident on the photodetector 226, resulting in a stronger measured signal.

Figure 13:
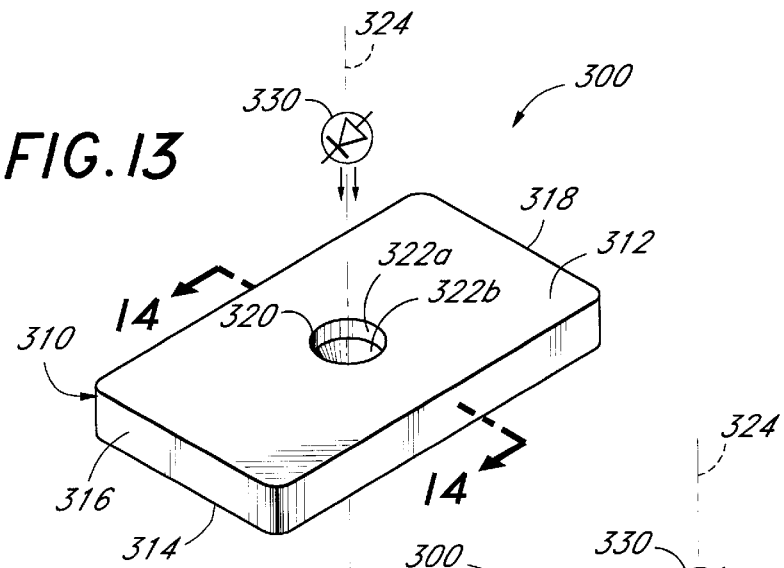
FIG. 13 is a perspective view of probe of the present invention having a three segment chamber.
Figure 14:
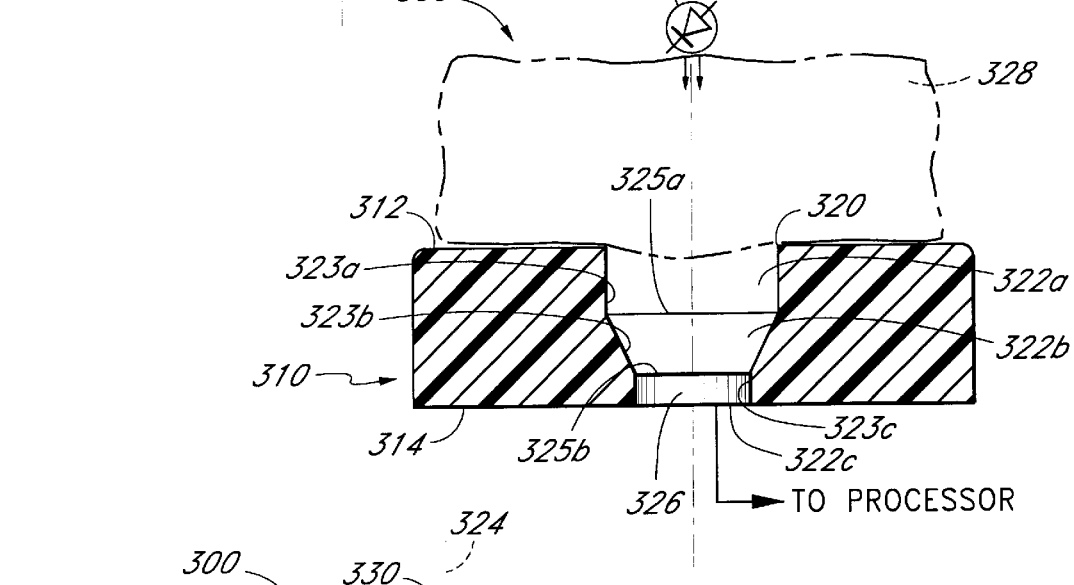
FIG. 14 is a cross-sectional view of the probe of FIG. 13 incorporating a three segment chamber having a detector within it.

A perspective view of another embodiment of the probe 300 of the present invention which incorporates a chamber 322 having three segments 322a, 322b, and 322c is shown in FIG. 13. The probe 300 has a base 310 with a top 312, a bottom 314, a forward end 316, and a rear end 318. The base 310 is typically made of rigid opaque material. However, it will be understood that the base 310 may be made of other materials which may be rigid, resilient, opaque, or transparent, for example. A cross-sectional view of the chamber 322 of this embodiment is shown in FIG. 14. For clarity in the perspective view of FIG. 13, a material 328 on which measurements are to be taken is not shown placed adjacent the probe 300. However, the material 328 is shown in the cross section of FIG. 13. An aperture 320 of any shape is formed in the base 310, similar to the apertures 120 and 220 described above. The aperture 320 forms the opening to a stabilizing segment 322a of a three segment chamber 322. A lateral cross-section (not shown) of the stabilizing segment 322a of the chamber 322 is typically the same shape as the aperture 320. Walls 323a of the stabilizing segment 322a are generally perpendicular to the aperture 320. A central axis 324 of the chamber 322 is defined by a line aligned perpendicular to the aperture 320 and extending generally through a central portion of the aperture 320 and the chamber 322.

A second, transitional segment 322b of the chamber 322 is adjacent the stabilizing segment 322a of the chamber 322. A top border 325a is formed between the transitional segment 322b and the stabilizing segment 322a of the chamber 322. The transitional segment 322b shares the same central axis 324 as the stabilizing segment 322a. Walls 323b of the transitional segment 322b are angled inwardly such that a bottom border 325b of the transitional segment 322b is of smaller dimension than the top border 325a of the transitional segment 322b.

The bottom border 325b of the transitional segment 322b leads into a mounting segment 322c of the chamber 322. The mounting segment 322c shares the same central axis 324 of the stabilizing and transitional segments 322a and 322b and is typically of smaller width than the stabilizing and transitional segments 322a and 322b. Walls 323c of the mounting segment 322c are generally parallel to the central axis 324. Thus, any cross-section of the mounting segment 322c cut perpendicular to the central axis 324 of the chamber 322 is typically of approximately the same shape as the bottom border 325b of the transitional segment 322b of the chamber 322. The mounting segment 322c may extend through the bottom 314 of the base 310, as shown. Alternatively, the mounting segment 322c may extend to just above the bottom 314 of the base 310, leaving a shell (not shown) of base 310 material at the bottom 314 of the three segment chamber 322.

A photodetector 326 is placed within the mounting segment 322c of the chamber 322, at the bottom 314 of the chamber 322 in the present embodiment. A central portion of the photodetector 326 is aligned with the central axis 324 of the chamber 322. The mounting segment 322c of the chamber 322 is deep enough that the photodetector 326 does not penetrate into the stabilizing segment 322 of the chamber 322. The photodetector 326 may be fixed within the chamber 322 according to a number of different methods, including but not limited to adhesive, a press fit, or a clear epoxy resin which transmits light over a range of wavelengths of interest. In this embodiment, the bottom 314 of the chamber 322 is made opaque via the press fit, paint, or tape, for example. The photodetector 326 is electrically connected to a processor, similarly to the photodetectors 126 and 226 in the previous embodiments of the probe of the present invention.

When a portion of an energy absorbing material 328 is placed over the probe 300, as shown in the cross-section of FIG. 14, it may rest above the chamber 322. Additionally, the stabilizing segment 322a of the chamber 322 is wide enough that easily compressible portions of the material 328 may enter into the stabilizing segment 322a of the chamber 322. The stabilizing segment 322a of the chamber 322 is deep enough that the easily compressible portion of the material 328 which intrudes into the stabilizing segment 322a does not contact matter within the stabilizing segment 322a which might cause compression of the material 328, even when the material 328 is caused to move. The chamber 322 shields the compressible material 328 from contact which might cause compression of the material 328 and thereby change the optical path length through the material 328.

An LED 330 is affixed to the material 328, opposite the aperture 320. The LED 330 is advantageously aligned along the central axis 324 to optimize the amount of light incident directly through the material 328 onto the photodetector 326. It will be understood that the positions of the photodetector 326 and the LED 330 could be interchanged as discussed in conjunction with FIG. 7. Additionally, a collimating lens assembly (not shown) could be added to the chamber 322 as discussed in conjunction with FIG. 8. The collimating lens assembly may be held in the chamber 322 similarly to a light collecting lens 332 discussed below. Further, it will be understood that the LED 330 and the photodetector 326 could be unaligned, as discussed in conjunction with FIG. 9.

As light from the LED 330 propagates through the material 328, it is scattered by the material 328 and is thus transmitted into the chamber 322 over a broad range of angles. Thus, some of the light is caused to be incident on the opaque walls 323a, 323b, and 323c of the chamber 322 and is absorbed. However, the advantageous alignment of the photodetector 326 and the LED 330 along the central axis 324 of the chamber 322 causes a large percentage of the light to be incident on the surface of the photodetector 326. Since the material 328 remains substantially uncompressed above and within the stabilizing segment 322a, the thickness through which the light travels, or the optical path length, is substantially stabilized. Thus, the signal-to-noise ratio of the measured signal is improved by the suppression of motion artifacts. Additionally helping to improve the signal to noise ratio of the measured signal is the opaque bottom 314 of the mounting segment 322c which shelters the photodetector 326 from ambient light.

Figure 15:
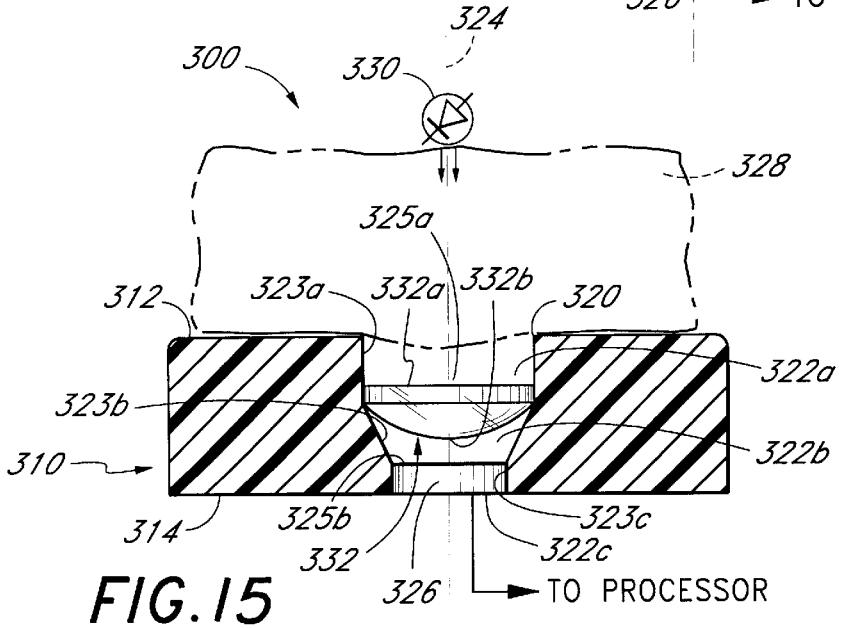
FIG. 15 is a cross-sectional view of another embodiment of the probe of FIG. 13 incorporating a light collimating lens.

In another embodiment of the probe 300 of the present invention, a light collecting lens 332 is added to the transitional segment 322b of the chamber 322, as shown in a cross sectional view in FIG. 15. The lens 332 is supported in the transitional segment 322b and may be held in the transitional segment 322b by a number of means, including but not limited to optical adhesive, a lens retaining ring, or a press fit. The lens has a generally planar surface 332a aligned with the top border 325a of the transitional segment 322b of the chamber 322 and a generally convex surface 325b extending into the transitional segment 322b of the chamber 322. The stabilizing segment 322a of the chamber 322 is deep enough that the lens 332 does not contact the easily compressible material 328 which rests above or has intruded into the chamber 322.

The lens 332 collects light which is incident on the planar surface 332a. Much of the light which is incident on this surface 332a at angles which would have been absorbed by the walls 323a, 323b and 323c of the chamber 322 if the lens 332 were not present is now directed toward the photodetector 326. Thus, a greater percentage of the light transmitted through the material 328 is caused to be incident on the photodetector 326, resulting in a stronger measured signal.

It will be understood that the walls 323b of the transitional segment 322b in each of the above described embodiments need not be sloped to achieve transition from larger width in the stabilizing segment 322a to smaller width in the mounting segment 322c. The walls 323b of the transitional segment 322b could be aligned generally parallel to the central axis 324, arranged at a distance which would cause the width of the transitional segment 322b to be less than the width of the stabilizing segment 322a and greater than the width of the mounting segment 322c.

FIG. 16 shows a perspective view of another probe 400 of the present invention specifically designed for use with a digit, such as a finger or a toe. For ease of illustration, the present example will pertain to a finger, though it will be understood that the present example could equally well pertain to any digit. FIG. 17 illustrates a schematic finger 428 comprising nail, skin, bone, tissue, muscle, blood, etc. Constituents in the finger's pad 404, such as fat and tissue, are easily compressible with motion of a patient. Even slight motion of the finger 428 can cause the thickness of constituents within the finger 428 to change greatly, thereby causing large motion induced excursions to occur in a measured signal, often obscuring a desired portion of the measured signal from which information about the patient can be determined.

As depicted in FIG. 16, base 410 of the finger probe 400, called a saddle 410 in this embodiment, is generally semi-cylindrical and preferably is made of a rigid or semi-rigid, opaque material such as black plastic. It will be understood, however, that the saddle 410 may be made of other materials, including those which are rigid, resilient, opaque, and transparent, for example. The saddle 410 has a top 412, a bottom 414, a forward end 416, a rear end 418, a ridge 440, and sidewalls 450 which curve upwardly from the ridge 440 to form a U-shape in cross-section, as shown in FIG. 18.

As illustrated in FIGS. 16 and 18, an aperture 420 forms the entrance to a chamber 422, located between one-quarter to one-half of the length of the saddle 410 from the forward end 416 of the saddle 410, as shown in the longitudinal cross-section of FIG. 19. The aperture 420 can be of any shape, including but not limited to circular, square, or triangular. The aperture 420 is the entrance to a chamber 422, as described previously in conjunction with other embodiments 100, 200, and 300 of the probe of the present invention. The chamber 422 may also be of any shape, including but not limited to circular, square, or triangular in cross-section.

The chamber 422 may have one or more segments, as described previously. Although the chamber 422 shown in this embodiment is a three segment chamber 422, having a stabilizing segment 422a, a sloped-wall transitional segment 422b, and a mounting segment 422c aligned on a common central axis 424, it will be understood that any chamber 422 which protects from compression, a compressible portion of the finger 428 through which light energy passes during absorption measurements, is a viable alternative. It will further be understood that a shell (not shown) of saddle 410 material could cover the bottom 414 of the chamber 422, as described previously with respect to the embodiment of the probe shown in FIG. 5.

A photodetector 426 is placed within the chamber 422, typically at the bottom 414 of the mounting segment 422c of the chamber 422. The photodetector 426 may be in place by adhesive, a press fit, or a clear epoxy resin which transmits light over a range of wavelengths of interest, for example. Typically, the bottom 414 of the chamber 422 is made opaque via tape or paint, for example, such that ambient light does not affect the photodetector 426.

The finger 428 is placed on the saddle 410, the finger pad 404 directly adjacent the aperture 420 and chamber 422. Additionally, the finger pad 404 may rest above the chamber 422. The aperture 420 and stabilizing segment 422a of the chamber 422 are wide enough that any easily compressible portion of the finger 428, such as a portion of the finger pad 404, may intrude into the chamber 422. The stabilizing segment 422a of the chamber 422 is deep enough that any portion of the finger 428 which does penetrate into the stabilizing segment 422a does not contact any matter within the stabilizing segment 422a which might cause compression of the finger 428, even when the finger 428 is caused to move.

An LED 430 is affixed to the finger 428, generally opposite the aperture 420. The LED 430 is typically attached to the finger 428 via adhesive, such as medical tape. The LED 430 is advantageously aligned along the central axis 424 to optimize the amount of light transmitted directly through the finger 428 onto the photodetector 426. However, it will be understood that the positions of the photodetector 426 and the LED 430 could be interchanged as discussed in conjunction with FIG. 7. Additionally, a collimating lens assembly (not shown) could be added to the chamber 422 as discussed in conjunction with FIG. 8. The collimating lens assembly may be held in the chamber 422 similarly to a light collecting lens 432 discussed below. Further, it will be understood that the LED 430 and the photodetector 426 could be unaligned, as discussed in conjunction with FIG. 9.

The LED 430 emits a light energy signal which propagates through the finger 428 and is transmitted into the chamber 422. The chamber 422 shields from compression the portion of the finger 428 through which light energy passes. Thus, the optical path length of the light through the finger 428 is substantially stabilized and motion artifacts are substantially reduced in the measured signal. It will be understood that a single segment chamber as described in conjunction with FIGS. 3 through 9 or a two segment chamber as described in conjunction with FIGS. 10 through 12 could equally well be used in the finger probe 400 of the present invention to shield the compressible portion of the finger 428 from compression and thereby reduce motion artifacts.

FIGS. 16, 18, and 19 illustrate a perspective view, a frontal cross-sectional view, and a longitudinal cross-sectional view, respectively, of one embodiment of the finger probe 400. The curvature of the saddle 410 is correlated to the average curvature of the finger 428 such that the sidewalls 450 form a semi-circular splint-type support for the finger 428. The saddle 410 is approximately 25 mm long between the forward end 416 and the rear end 418, such that a portion of the finger 428 between its tip 406 and approximately its first knuckle 408 (shown in FIG. 17) fits between the front 416 and the rear 418 ends of the probe 400. The curvature of the saddle 410 is generally defined by a line 460 (shown in FIG. 18) which is tangent to a sidewall 450 at an angle between 30° and 50° from horizontal.

The placement of the aperture 420 at a point between one-third and one-half of the length of the saddle 410, causes the thickest section of the compressible portion of the finger 428, or the finger pad 404, to rest above and within the chamber 422. Thus, the portion of the finger 428 with the greatest amount of compressible material is safeguarded from compression by the chamber 422.

In the embodiment of the finger probe 400 shown in FIGS. 16, 18, 19, and 20, the aperture 420 is generally circular and the chamber 422 has three segments 422a, 422b, and 422c, as shown in the cross-sectional view of FIG. 18. Advantageously employed dimensions for the finger probe 400 illustrated in FIGS. 16, 18, 19, and 20 include the stabilizing segment 422a of the chamber 422 being generally cylindrical and having a diameter of approximately seven millimeters. Additionally, the stabilizing segment 422a of the chamber 422 is deep enough that any portion of the finger 428 which penetrates into the chamber remains substantially free of perturbation, even when the finger 428 moves. An advantageous depth for the stabilizing segment 422a is thus approximately two millimeters deep. The mounting segment 422c of the chamber 422 is also cylindrical, having a diameter of approximately five millimeters. The transitional segment 422b of the chamber 422 is of varying diameter, having sloped walls 423b, such that a top border 425a is approximately seven millimeters in diameter and a bottom border 425b is approximately five millimeters in diameter. A detector 426 having up to a 5 millimeter diameter is positioned in the bottom 416 of the mounting segment 422c of the chamber 422.

In another embodiment of the finger probe 400, a light collecting lens 432 may be added to the finger probe 400 of the present invention, as shown in FIG. 20. The saddle 410 and the chamber 422 function as discussed above. The lens 432 functions as described above in conjunction with FIGS. 6, 12, and 15 to collect light incident on the lens 432 which would be absorbed by the walls 423a, 423b and 423c of the chamber 422 if the lens 432 were not present. Thus, a greater percentage of the light transmitted through the finger 428 is directed onto the photodetector 426, resulting in a stronger measured signal.

Other embodiments of the probe of the present invention may be specifically designed and manufactured for use with an earlobe or other thin section of the body, such as a nostril or a lip, using the principles described herein. Also, embodiments of the probe of the present invention utilizing the properties of attenuation as energy is reflected from a medium, rather than transmitted through a medium, may be made using similar principles.

A probe 700 specifically designed to measure reflected energy is shown in cross-section in FIG. 21. A base 710 is placed adjacent a material 728 on which reflectance measurements are to be made. A photodetector 726 and an LED 730 are located within the base 710. In the embodiment shown in FIG. 21, the photodetector 726 is positioned within a chamber 722x and the LED 730 is positioned within a chamber 722y. Although single segment chambers 722x and 722y are illustrated, the chambers 722x and 722y may be of any suitable shape and size. The chambers 722x and 722y function to stabilize the optical path length, as discussed previously, by shielding from compression any compressible portion of a material which rests above or intrudes into the chambers 722x and 722y.

A light collecting lens (not shown) may be added to the chamber 722x having the photodetector 726 within it, as discussed previously in conjunction with FIGS. 6, 12 and 15. Additionally, a collimating lens assembly (not shown) may be added to the chamber 722y having the LED 730 in it, as discussed previously in conjunction with FIG. 8. The chambers 722x and 722y may be formed with or without a shell (not shown) of base 710 material, as discussed previously in conjunction with FIG. 5.

It will be understood that in other embodiments (not shown) of the reflectance probe 700, the photodetector 726 could protrude from the base 710 and the LED 730 be located within a chamber 722y or the LED 730 could be protrude from the base 710 and the photodetector 726 could be located within a chamber 722x. Additionally, the photodetector 726 and the LED 730 could be located within a single chamber 722. In any embodiment the chamber(s) 722 may have any number of segments of any suitable shape.

The type of probe 700 which relies on reflection may be advantageously utilized on materials where a photodetector 726 and an LED 730 cannot be placed on opposite sides of the material 728, such as with the forehead. However, a reflectance probe 700 can be used anywhere a non-invasive measurement needs to be taken, such as a lip, an earlobe, or a finger, for example.

FIG. 22 shows a cross-sectional view of another probe 800 of the present invention wherein two bases 810x and 810y are placed adjacent to a material 828 on which measurements are to be made. The bases 810x and 810y are located on opposite sides of the material 828. A photodetector 826 is placed in a chamber 822x in the base 810x. An LED 830 is placed in a chamber 822y in the base 810y. The photodetector 826 and the LED 830 are aligned substantially along a central axis 824. Although two segment chambers 822x and 822y are illustrated, the chambers 822x and 822y may be of any suitable shape and size. Independent of which shape of chamber is utilized, the chambers 822x and 822y function to stabilize the optical path length and thereby reduce the effects of motion artifacts on the measured signals.

As discussed previously, the probe 800 may be modified slightly with a light collecting lens (not shown) added to the chamber 822x with the photodetector 826 in it. A collimating lens assembly (not shown) may be added to the chamber 822y with the LED 830 in it. Additionally, the chambers 822x and 822y may be formed with or without a shell (not shown) of base 810x and 810y material. The probe 800 is particularly advantageous when a material 828 is compressible on more than one side since each chamber 822x and 822y supports and shields from compression any compressible portion of a material 828 which rests above or intrudes into the chambers 822x and 822y, respectively.

FIG. 23 shows a cross-sectional view of another probe 900 of the present invention wherein a chamber 922 having walls 923 is formed to concentrate, or "funnel," energy onto the surface of a photodetector 926. An aperture 920 is formed in a base 910, the aperture 920 leading to a generally cone-shaped chamber 922. The base 910 is placed adjacent a material 928 on which measurements are to be made, the chamber 922 being placed directly adjacent any easily compressible portion of the material 928. The photodetector 926 is placed within the chamber 922, typically at the bottom of the chamber 928. A light emitting diode 930 is placed on the material 928, generally opposite and aligned with the photodetector 926.

As discussed previously, a portion of the material 928 is supported by the area surrounding the aperture 920. Additionally, the aperture 920 and chamber 922 are wide enough that any easily compressible portion of the material 928 may intrude into the chamber 922 without being compressed, thereby shielding this portion of the material 928 from compression, even during motion of the material 928. This substantially stabilizes the optical path length and improves the signal to noise ratio of the signal measured at the photodetector 926.

Further improving the signal to noise ratio of measurements made with the probe 900, reflective material, such as a highly reflective metal, covers the walls 923 of the chamber 922. This causes light scattered by the material 928 and made incident on the walls of the chamber 922 to be reflected. The cone shape causes the light to be concentrated generally on the photodetector 926.

Depending upon the shape of the photodetector 926, the chamber 922 may be advantageously contoured to maximize the funneling of light onto the photodetector 926. If the photodetector 926 is flat, the chamber is most advantageously shaped having a generally hyperbolic cross-section. However, if the photodetector 926 is spherical or slightly curved, as is often the case due to manufacturing processes, the chamber is most advantageously shaped having a cone-shaped cross-section with uncurved walls 923.

As discussed previously in conjunction with other embodiments of the probe of the present invention, the probe 900 may be modified to include a light collecting lens (not shown). Alternatively, an LED 930 could be placed within the chamber 922 instead of the photodetector 926. With the LED in the chamber 922, a collimating lens assembly (not shown) could be placed within the chamber 922. Two bases 910 with two generally cone-shaped chambers could be utilized on one or either side of a material 928. A single base 910 with two generally cone-shaped chambers 922 located side by side could also be used for reflective measurements. Additionally, the photodetector 926 and the LED 930 need not be aligned along the central axis 924.

Figure 24:
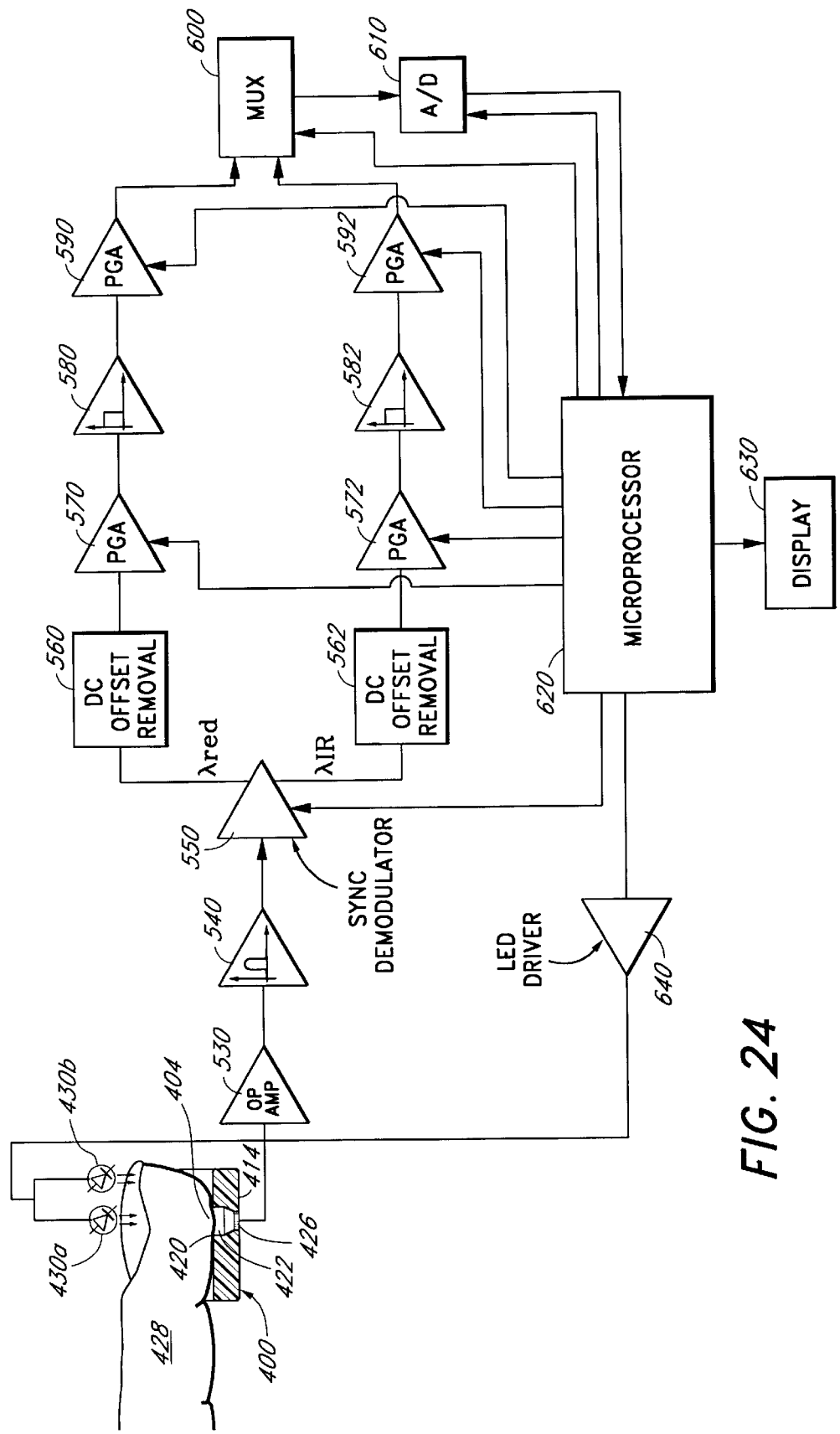
FIG. 24 is a schematic of one system which may advantageously employ a probe of the present invention.

FIG. 24 depicts one embodiment of a probe constructed in accordance with the present invention coupled to an oximeter. The oximeter could be any oximeter known in the art which utilizes light attenuation measurements. A block diagram of one possible oximeter is depicted in FIG. 24. The oximeter shown in FIG. 24 is a pulse oximeter wherein the finger probe 400 is employed and two measured signals at different wavelengths, one of which is typically red and the other of which is typically infrared, are alternately passed through the finger 428. Signals measured at the photodetector 426 are then processed to determine the amount of oxygen available to the body. This is evaluated by finding the saturation of oxygenated hemoglobin in blood comprising both oxygenated and deoxygenated hemoglobin.

Two LEDs 430a and 430b, one LED 430a emitting red wavelengths and another LED 430b emitting infrared wavelengths, are placed adjacent the finger 428. The finger probe 400 is placed underneath the finger 428, the aperture 420 and chamber 422 located directly adjacent the finger pad 404. The photodetector 426 in the bottom 414 of the chamber 422 is connected to a single channel of common processing circuitry including an amplifier 530 which is in turn connected to a band pass filter 540. The band pass filter 540 passes signal into a synchronized demodulator 550 which has a plurality of output channels. One output channel is for signals corresponding to visible wavelengths and another output channel is for signals corresponding to infrared wavelengths.

The output channels of the synchronized demodulator 550 for signals corresponding to both the visible and infrared wavelengths are each connected to separate paths, each path comprising further processing circuitry. Each path includes a DC offset removal element 560 and 562, such as a differential amplifier, a programmable gain amplifier 570 and 572 and a low pass filter 580 and 582. The output of each low pass filter 580 and 582 is amplified in a second programmable gain amplifier 590 and 592 and then input to a multiplexer 600.

The multiplexer 600 is connected to an analog-to-digital converter 610 which is in turn connected to a microprocessor 620. Control lines between the microprocessor 620 and the multiplexer 600, the microprocessor 620 and the analog-to-digital converter 610, and the microprocessor 620 and each programmable gain amplifier 570, 572, 590, and 592 are formed. The microprocessor 620 has additional control lines, one of which leads to a display 630 and the other of which leads to an LED driver 640 situated in a feedback loop with the two LEDs 430a and 430b.

Each of the LEDs 430a and 430b alternately emits energy which is absorbed by the finger 428 and received by the photodetector 426. The photodetector 426 produces an electrical signal which corresponds to the intensity of the light energy striking the photodetector 426 surface. The amplifier 530 amplifies this electrical signal for ease of processing. The band pass filter 540 then removes unwanted high and low frequencies. The synchronized demodulator 550 separates the electrical signal into electrical signals corresponding to the red and infrared light energy components. A predetermined reference voltage, $V_{ref}$, is subtracted by the DC offset removal element 560 and 562 from each of the separate signals to remove substantially constant absorption which corresponds to absorption when there are no motion artifacts. Then the first programmable gain amplifiers 570 and 572 amplify each signal for ease of manipulation. The low pass filters 580 and 582 integrate each signal to remove unwanted high frequency components and the second programmable gain amplifiers 590 and 592 amplify each signal for further ease of processing.

The multiplexer 600 acts as an analog switch between the electrical signals corresponding to the red and the infrared light energy, allowing first a signal corresponding to the red light to enter the analog-to-digital convertor 610 and then a signal corresponding to the infrared light to enter the analog-to-digital convertor 610. This eliminates the need for multiple analog-to-digital convertors 610. The analog-to-digital convertor 610 inputs the data into the microprocessor 620 for calculation of the saturation of oxygen according to known methods, such as those described in U.S. patent application Ser. No. 07/666,060 filed Mar. 7, 1991, and abandoned in favor of continuation U.S. patent application Ser. No. 08/249,690, entitled "SIGNAL PROCESSING APPARATUS AND METHOD," filed May 26, 1994, both assigned to MASIMO CORPORATION, the same assignee as the present patent, and incorporated herein by reference. The microprocessor 620 centrally controls the multiplexer 600, the analog-to-digital convertor 610, and the first and second programmable gain amplifiers 570, 590, 572, and 592 for both the red and the infrared channels. Additionally, the microprocessor 620 controls the intensity of the LEDs 430a and 430b through the LED driver 640 in a servo loop to keep the average intensity received at the photodetector 426 within an appropriate range.

As explained above, the probe of the present invention could be used with a variety of oximeter systems. A recent embodiment of an oximeter by the assignee of the present application is described in detail in U.S. patent application Ser. No. 08/320,154, entitled "Signal Processing Apparatus," and filed Oct. 7, 1994, which patent application is also incorporated herein by reference.

Figure 25:
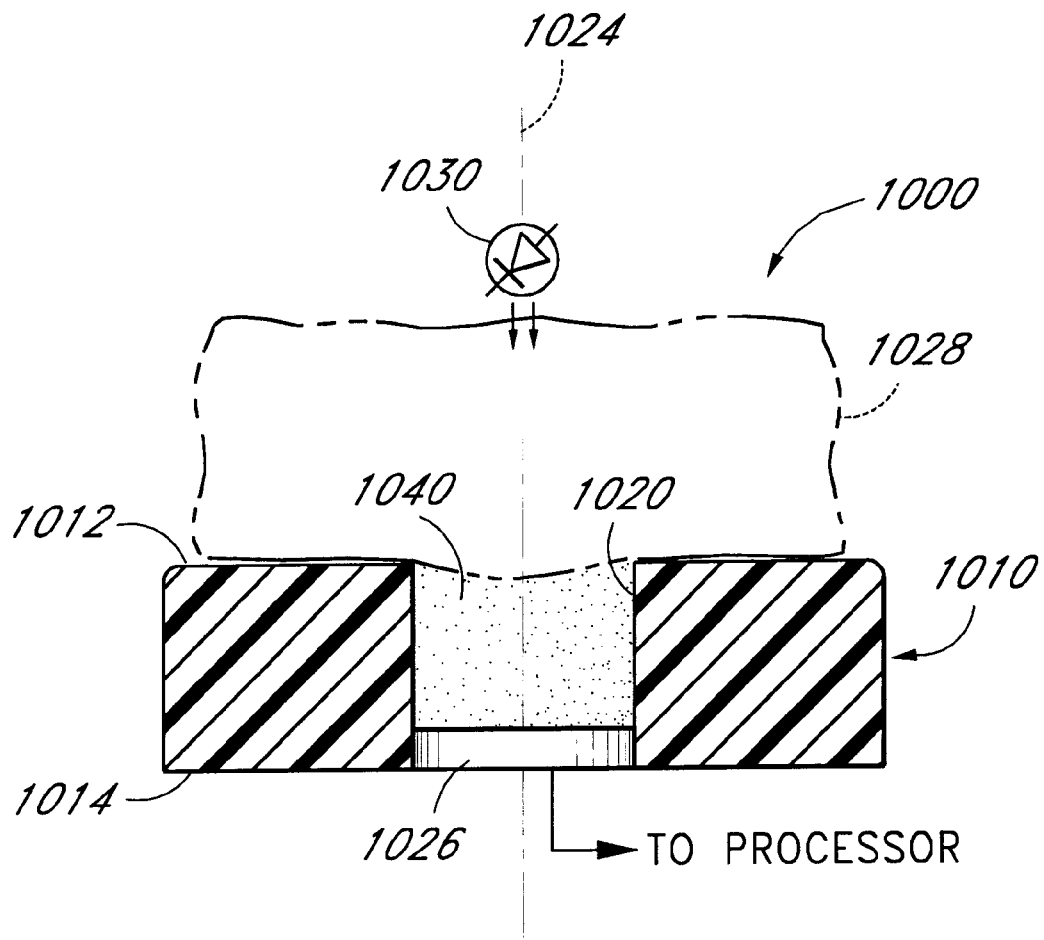
FIG. 25 is a cross-sectional view of a probe wherein the aperture is filled with a compressible scattering medium.

FIGS. 25–28 depict alternative embodiments of the present invention wherein an improved signal to noise ratio is observed in the received signal due to optical scattering effects. A probe 1000, shown in cross-section in FIG. 25, includes a base 1010, having a top 1012, a bottom 1014, and a forward and a rear end (not shown in FIG. 25). The base 1010 is preferably rigid and opaque to the wavelengths used in the probe 1000. An aperture 1020 is formed in the top 1012 of the base 1010. The aperture 1020 may be cylindrical (as shown in FIG. 25), conical, rectangular, or other shapes as called for by the specific application. The depth of the aperture 1020 may, for example, range from 0.5 mm to 10 mm, and is preferably in the range of 2–4 mm in depth in one embodiment, and more preferably in the range of 3–4 mm. Furthermore, the diameter of the aperture 1020 may range from 3 mm to 20 mm, as called for by the specific application. It has been found by the inventors that an aperture less than 0.5 mm in diameter does not obtain the benefits of the present invention.

A light source 1030 (e.g., one or more light emitting diodes) is affixed adjacent to material 1028 (e.g., an earlobe, finger, or other fleshy material), aligned along a central axis 1024 which passes substantially through the center of a photodetector 1026. The aperture 1020 is filled wholly, or in part, by a scattering medium 1040, which may, for example, comprise 2.2 pound polyurethane reticulated foam (although conformable plastic or scattering gels may also be employed). In general, the scattering medium may comprise one of a number of fixotropic materials (i.e., materials having two or more mixed materials which are conducive to scattering). Ideally, the scattering medium 1040 scatters but does not significantly absorb optical radiation at the operational red (e.g., 660 nm) and infrared (e.g., 940 nm) wavelengths for the oximeter. In other words, the material is clear to optical absorption, but still scatters light.

In operation, the light source 1030 (e.g., two LEDs in the present embodiment) emits optical radiation (e.g., in the red or infra-red spectrum range) which passes through the material under test 1028. The optical radiation is received by the photodetector 1026 after passing through the scattering medium 1040. The received optical radiation is scattered by the scattering medium 1040.

The scattering of the optical radiation within the scattering medium 1040 has been found to increase the signal-to-noise ratio of the received signal. It is believed that the signal-to-noise ratio is improved because there appears to be a reduced effect on the signal from any particular local region of the material 1028 (e.g., flesh). That is, by scattering the signal either prior to or posterior to the material interface, the signal is effectively spread over a larger area of the material 1028. Thus, perturbations of a locality within the area of exposure will have less effect with a scattered beam over a large area than with a more concentrated signal passing through that same locality. In this way, the effect of perturbations on the average signal is reduced.

The scattering medium 1040 should be soft (i.e., highly compressible) so that the material 1028 does not significantly compress when the material 1028 presses against the scattering medium 1040. Compression of the scattering medium 1040 does not significantly alter the amplitude of the measured signal since the scattering medium is not highly absorbtive of the optical radiation. Furthermore, although conformable plastics may be used, reticulated foams are preferred since reticulated foams provide improved optical coupling with flesh. This is because the reticulated foam provides contact in spots rather than across large areas of the flesh. If contact is made across large areas of flesh, microscopic droplets of perspiration or oil can form a layer between the flesh and the scattering medium 1040. This layer creates an impedance mismatch interface which is absorbtive of the optical radiation. Of course, gels may also be used in accordance with the present invention. Such gels should not contain significant amounts of metal salts or silica because these materials absorb light.

The teachings of the present invention depart from conventional methods of improving optical signal-to-noise ratios. Commonly, lens assemblies which focus optical radiation are used to improve the signal-to-noise ratios of optical signals. However, oximetry by means of transmission or reflection is a non-imaging method of optical detection. Thus, the form of the image is not important for detection purposes. For this reason, scattering may be used as a method of improving optical signal quality; whereas, since scattering was thought to degrade signal-to-noise ratios of optical signals, previous methods have not employed optical scattering techniques.

Figure 26:
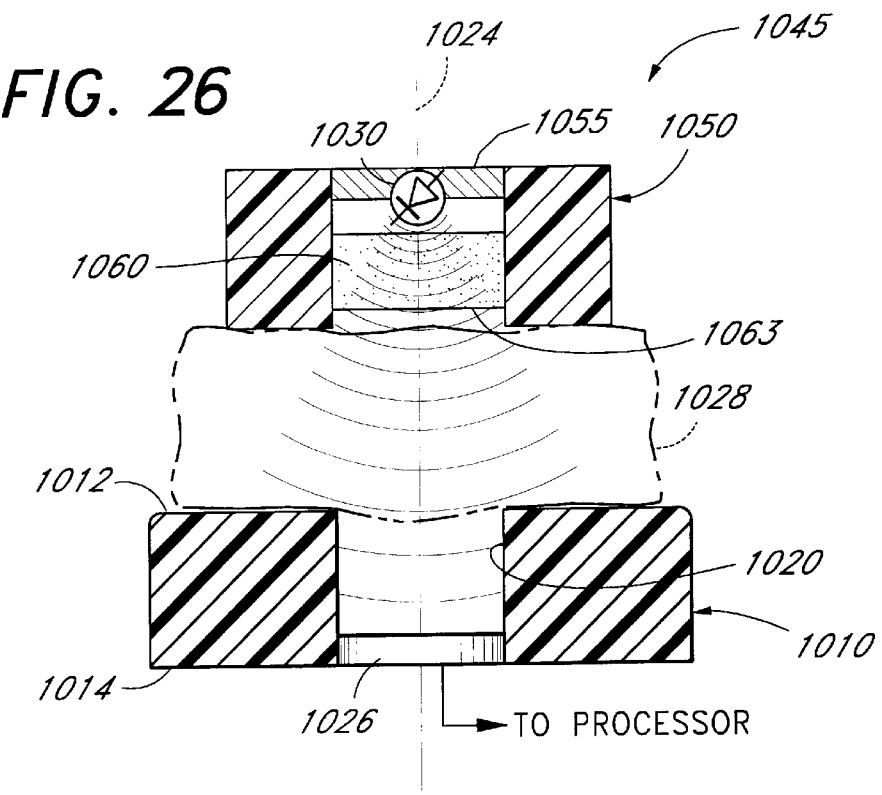
FIG. 26 is a cross-sectional view of a probe wherein the LED is spaced from the material to be measured by a transmission assembly having a scattering medium interposed between the LED and the material.
Figure 27:
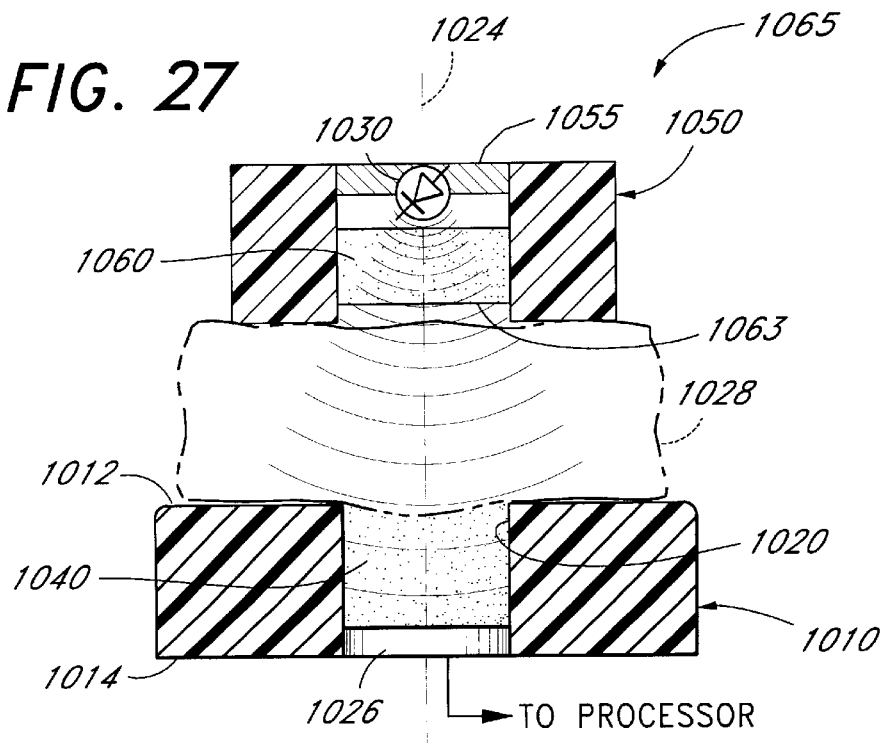
FIG. 27 is a cross-sectional view of a probe wherein a scattering medium is interposed between the LED and the material as well as between the material and the photodetector.

FIGS. 26 and 27 depict further alternative embodiments of the present invention wherein optical scattering is provided prior to the flesh interface, and both prior and posterior to the flesh interface, respectively. In FIG. 26, an oximetry probe 1045 further has a transmission assembly 1050 which secures the LED 1030 in place within a backing 1055. A scattering medium 1060, having a face 1063, is interposed between the LED 1030 and the material 1028. In the embodiment depicted in FIG. 26, the scattering medium 1060 does not contact the LED 1030; however, it should be understood that the scattering medium 1060 may contact one or both of the LED 1030 and the material 1028.

The scattering medium 1060 diffuses the optical radiation emitted by the LED 1030 over a wider area. Thus, the LED 1030, which is essentially a point source, is transformed into an evenly distributed source of light over the entire area of the face 1063 of the scattering medium 1060. The diffusion of the light over a wider area provides an improved signal-to-noise ratio.

Figure 28:
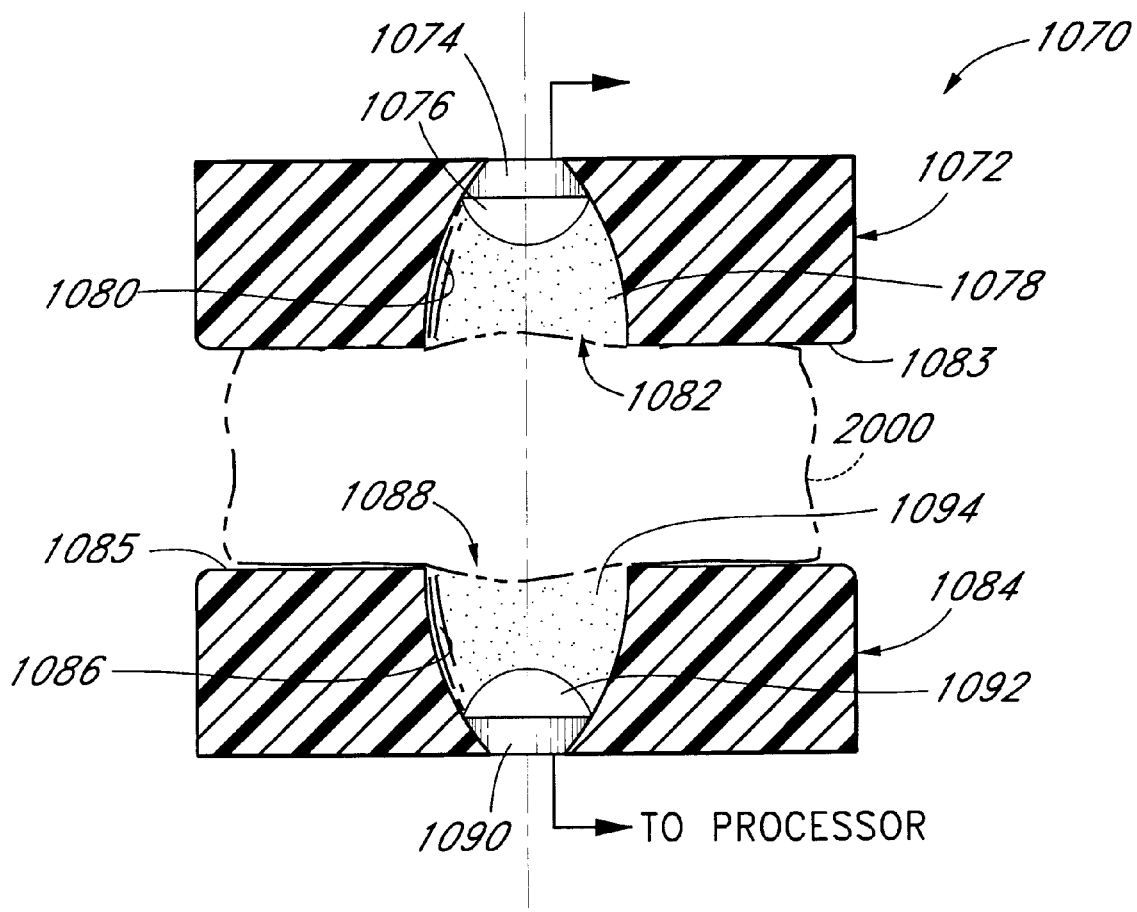
FIG. 28 is a cross-sectional view of a preferred embodiment of a probe in accordance with the present invention having an immersion lens for the photodetector and for the LED and having scattering medium interposed between the LED and the test material as well as between the test material and the photodetector.

As seen in FIGS. 26–28, the light is scattered. This is represented by the energy intensity contours rather than light path indicators. As recognized by the present inventors, the particular light path is not significant. The important aspect is the intensity of the light and the field of view of the photodetector and the light source. This will be explained further in connection with the embodiment of FIG. 28 utilizing an immersion lens.

The operation of a probe 1065 shown in FIG. 27 is essentially the same as that of the probe 1045, with the exception that the scattering medium 1040 is provided within the aperture 1020. It has been found that by providing a scattering medium on both sides of the material 1028, an improved signal-to-noise ratio is observed over the probes having a scattering medium on only one side of the material 1028.

FIG. 28 depicts a preferred embodiment of a probe 1070 in accordance with the present invention. As depicted in FIG. 28, the probe 1070 comprises a transmission assembly 1072, having a light source 1074, an immersion lens 1076, scattering medium 1078, a chamber 1080 defining an aperture 1082 along a support surface 1083 of the transmission assembly. A detector assembly 1084 is similarly configured with a support surface 1085, a chamber 1086 defining an aperture 1088 along the support surface 1085, a photodetector 1090, an immersion lens 1092 and scattering medium 1094. FIG. 28 further depicts a test material 2000 such a human tissue (e.g., a finger or earlobe) interposed between the light source assembly 1072 and the detector assembly 1084.

Several advantages are obtained from the particular configuration shown in FIG. 28. First, it should be understood that an economical way to fabricate the light source in the photodetector is to utilize small semiconductor LEDs and photodetectors. Such devices are very small, and therefore, have a very small field of view. The inventors have recognized that it is advantageous to improve the field of view of the photodetector and the LED because the surface of the tissue material 2000 at the aperture of the support surfaces is large compared to the surface of the semiconductor photodetector and LED. Thus, without enlarging the field of view of the photodetector and/or LED, much of the tissue material interface at the apertures is not utilized. As explained above, scattering of the light improves the received signal quality. An immersion lens for the photodetector and/or LED increases the field of view of the semiconductor photodetector and LEDs such that a substantial portion of the tissue material covering the apertures is within the field of view of the photodetector and/or LED.

Because imaging optics are not required due to the advantages of scattering, a significantly advantageous configuration is to utilize epoxy placed directly over the photodetector and/or over the LED in the form of a partial sphere which performs suitably as an immersion lens in the present embodiment. In one embodiment, the index of refraction of the epoxy is advantageously 1.56. The epoxy also acts to protect the photodetector and/or LED. The immersion lens can be formed by placing a bump of epoxy over the photodetector and the LED.

The immersion lens formed by a bump of epoxy over the photodetector and/or LED expands the field of view for the photodetector and LED in order to disperse the transmitted light energy over the tissue surface area at the apertures which is large relative to the surface of the optical elements. This assists in minimizing the effects of the relatively small optical details of the test materials (e.g., pores, fingerprint lines, sweat glans).

In the advantageous embodiment of FIG. 28, the scattering material 1080, 1086 is also placed in the chambers 1080, 1086 in order to enhance scattering of the light as explained above.

The cone shaped chambers 1080, 1086 depicted in FIG. 28 are also advantageous when the walls of the chambers are coated with a highly reflective material which does not absorb the light from the LED. The cone shape assists in reflecting the light energy away from the LED and toward the photodetector. All of these elements in combination form a particularly advantageous probe which can maximize the signal-to-noise ratio of the probe and minimize the effects of motion artifact on the received signal.

It should be understood that in alternative embodiments of the probe 1070 depicted in FIG. 28, elements could be removed and still obtain significant benefit. For instance, the detector assembly 1084 could remain the same with the light source assembly 1072 simply becoming an LED with no support surface and no chamber. Alternatively, the scattering media 1078, 1086 could be removed from either the chamber 1080 in the light source assembly 1072 or the chamber 1086 in the detector assembly 1082.

One skilled in the art will realize that the light collecting lens, or other optical elements, could also be added to the chamber in any optical probe of the present invention to direct light onto the photodetector. However, the immersion lens provides better performance. One skilled in the art will further realize that the location of the photodetector and the LED may be interchanged in any of the above described probes. One skilled in the art will realize that the bottom of any chamber formed in a base of an optical probe of the present invention can remain exposed, be covered by a material such as opaque tape, or be covered by a shell of base material without affecting the reduction of motion artifacts brought about by the chamber. Additionally, one skilled in the art will realize that reflective measurements could be made with the probes of the present invention by mounting both the photodetector and LED on the base of the probe. Also, one skilled in the art will realize that a plurality of LEDs or photodetectors could be mounted in the chamber or affixed to the material such that more than one signal may be measured at a time. Furthermore, one skilled in the art will realize that any material having a chamber, with a detector or an LED mounted within the chamber, will reduce the effects of motion artifacts in non-invasive absorption (or reflection) measurements, according to the present invention.

It will be understood that the probe of the present invention may be employed in any circumstance where a measurement of transmitted or reflected energy is to be made, including but not limited to measurements taken on a finger, an earlobe, a lip, or a forehead. Thus, there are numerous other embodiments which will be obvious to one skilled in the art, including but not limited to changes in the shape of the probe, changes in the materials out of which the probe is made including rigid and resilient materials, and changes in the shape, dimensions, and location of the chamber. Moreover, the chamber(s) may be coated, in whole or in part, with reflective material to help direct energy onto the detector. Furthermore, the probe of the present invention may be employed in measurements of other types of energy. Depending upon the type of energy which is most advantageously utilized in a measurement, the type of transmitter or receiver of energy may be changed. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An oximeter sensor for measuring electromagnetic energy which has been attenuated by a living flesh material, said sensor comprising:

a light source;

a base having a thickness, said base being positioned adjacent said flesh material when said optical probe is positioned for use;

an aperture in said base, said aperture forming an entrance to a chamber which extends into said base, said aperture and chamber having a width of at least 3 mm and, said chamber having a particular depth such that the flesh material which penetrates into the chamber via said aperture is not substantially compressed with change in pressure between said flesh material and a surface defining said aperture typically expected from a patient; and a detector located within said chamber such that when said oximeter sensor is in use, said detector and light source are generally in axial alignment for transmission, said detector separated from any of said portion of flesh material which has penetrated into said chamber, said detector receiving electromagnetic energy transmitted by said light source and through said flesh material, said detector operative to generate a signal in response to said electromagnetic radiation, said width of said aperture being sized to reduce motion artifacts in said signal due to motion typically expected for a living patient.

2. The oximeter sensor of claim 1, wherein said light source is a light emitting diode configured to transmit light energy through said flesh material to said detector.

3. The oximeter sensor of claim 1, further comprising a pulse oximeter system having a pulse oximeter connected to said detector and responsive to the intensity of the electromagnetic energy transmitted through said flesh material and received by said detector to calculate the saturation of oxygen within the blood in the living flesh material.

4. A method of making a motion artifact resistant oximeter sensor, said method comprising the steps of:

forming a chamber having an aperture and sizing said aperture with width large enough such that a compressible portion of living tissue material when covering said aperture may enter said chamber when said sensor is in use, said chamber sized to substantially reduce motion artifact with changes in pressure between said tissue material in the area about said aperture expected due to patient movement;

locating a detector in said chamber in a position to detect electromagnetic energy which passes through a portion of tissue material covering the aperture of said chamber, said detector positioned so as not to contact said portion of tissue material; and locating an electromagnetic energy source on said oximeter sensor such that it is generally in axial alignment of transmission with said detector when said oximeter sensor is in use.

5. The method of claim 4, wherein said width is at least 10 millimeters.

6. The method of claim 4, wherein said width is at least 5 millimeters.

7. The method of claim 6, wherein said width is about 7 millimeters.

8. A method of stabilizing the optical path length through living flesh between a light source and a detector in an optical probe wherein the optical probe has a base and the detector is located in a chamber in the base that opens through an aperture to a surface of the base, said optical probe configure to be attached to flesh of a living subject, the method comprising:

selecting the size of said aperture so that a portion of the surface of the living flesh through which the light will pass, when said optical probe is attached to flesh of said living subject, will protrude substantially uncompressed into the detector chamber upon motion typically expected for a living patient and so that the size of the aperture substantially reduces motion artifact; and affixing the probe to the living flesh so that the said portion of the surface of the living flesh which protrudes into the chamber and the base moves with the movement, if any, of the adjacent living flesh.

9. An optical probe in accordance with claim 7, wherein the probe is sized and shaped to create an optical path through a finger.

* * * * *